(12) United States Patent
Ashford, II et al.

(10) Patent No.: US 11,561,220 B2
(45) Date of Patent: Jan. 24, 2023

(54) ELECTRODE FOR ELECTROCHEMICAL SENSORS

(71) Applicant: EASTMAN CHEMICAL COMPANY, Kingsport, TN (US)

(72) Inventors: Dennis Lee Ashford, II, Johnson City, TN (US); Spencer Erich Hochstetler, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 689 days.

(21) Appl. No.: 16/484,884

(22) PCT Filed: Jan. 30, 2018

(86) PCT No.: PCT/US2018/015851
§ 371 (c)(1),
(2) Date: Aug. 9, 2019

(87) PCT Pub. No.: WO2018/148052
PCT Pub. Date: Aug. 16, 2018

(65) Prior Publication Data
US 2019/0376960 A1  Dec. 12, 2019

Related U.S. Application Data

(60) Provisional application No. 62/457,627, filed on Feb. 10, 2017.

(51) Int. Cl.
*G01N 33/543* (2006.01)
*A61B 5/145* (2006.01)
(Continued)

(52) U.S. Cl.
CPC ....... *G01N 33/5438* (2013.01); *A61B 5/1468* (2013.01); *A61B 5/1477* (2013.01);
(Continued)

(58) Field of Classification Search
None
See application file for complete search history.

(56) References Cited

U.S. PATENT DOCUMENTS 4,345,985 A  8/1982  Masayuki et al.
4,536,274 A  8/1985  Papadakis et al.
(Continued)

FOREIGN PATENT DOCUMENTS

CN  103103572 A  5/2013

OTHER PUBLICATIONS

Macfie, Gavin et al, "Mechanism of 2-Mercaptoethanesulphonate Adsorption onto Sputtered Palladium Films: Influence of Surface Oxide Species", The Journal of Physical Chemistry C, 2012, 116, pp. 9930-9941.

(Continued)

*Primary Examiner* — J. Christopher Ball
(74) *Attorney, Agent, or Firm* — Michael K. Carrier; Robert C. Morriss

(57) ABSTRACT

An electrochemical electrode for use in a biosensor. The electrode comprises a substrate, a palladium metal layer manufactured on the substrate, and a palladium oxide-containing layer manufactured on the palladium metal layer. The palladium metal layer has a thickness of no more than 90 nm, and the palladium oxide-containing layer has a thickness of no more than 40 nm.

19 Claims, 12 Drawing Sheets

(51) Int. Cl.
| | |
|---|---|
| *C23C 14/08* | (2006.01) |
| *C23C 14/14* | (2006.01) |
| *C23C 14/34* | (2006.01) |
| *G01N 27/30* | (2006.01) |
| *G01N 27/327* | (2006.01) |
| *A61B 5/1468* | (2006.01) |
| *A61B 5/1477* | (2006.01) |

(52) U.S. Cl.
CPC .......... *A61B 5/14532* (2013.01); *C23C 14/08* (2013.01); *C23C 14/14* (2013.01); *C23C 14/34* (2013.01); *G01N 27/30* (2013.01); *G01N 27/327* (2013.01); *G01N 33/54393* (2013.01)

(56) References Cited

U.S. PATENT DOCUMENTS

| | | |
|---|---|---|
| 2009/0294277 A1 | 12/2009 | Thomas et al. |
| 2012/0183679 A1 | 7/2012 | Chen |
| 2016/0169827 A1 | 6/2016 | Hochstetler et al. |

OTHER PUBLICATIONS

Macfie Gavin et al, "Room temperature formation, electro-reduction and dissolution of surface oxide layers on sputtered palladium films", Science Direct, Oct. 1, 2011, vol. 56, Issue 24, pp. 8394-8402.

Notification of Transmittal of the International Search Report and the Written Opinion of the International Searching Authority, or the Declaration dated Mar. 20, 2019 received in International Application No. PCT/US2018/015851.

Qin, Yiheng et al, "Low-temperature solution processing of palladium/palladium oxide films and their pH sensing performance", Talanta, Sep. 11, 2015, vol. 146, pp. 517-524.

Mahbubur, Rahman et al, "A comprehensive review of glucose biosensors based on nanostructured metal-oxides", Sensors, Jan. 1, 2010, vol. 10, No. 5, pp. 4855-4886.

Zheng, et al., The Oxidation Mechanism of Pd(100), Elsevier, Surface Science 504, 2002, pp. 253-270.

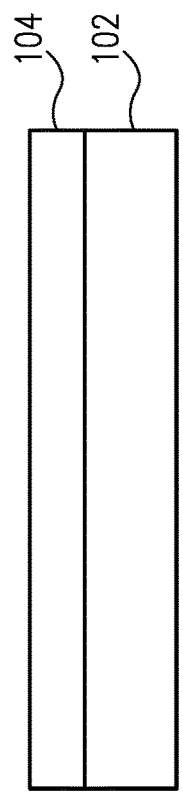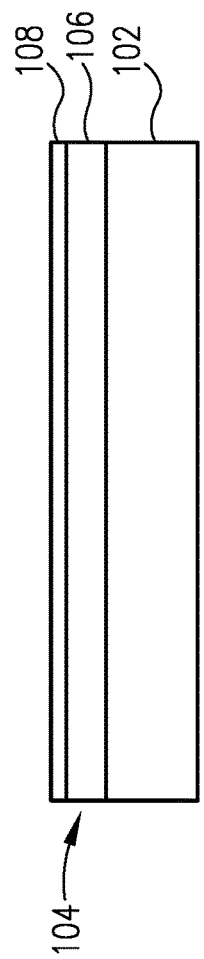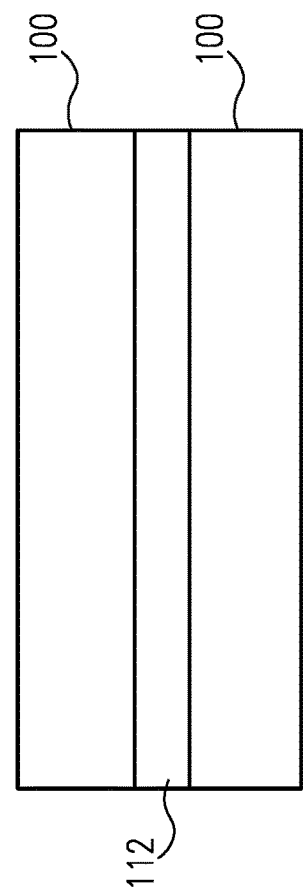

ELECTRODE FOR ELECTROCHEMICAL SENSORS

CROSS-REFERENCE TO RELATED APPLICATION(S)

This application is a national stage filing under 35 USC § 371 of International Application Number PCT/US2018/015851, filed on Jan. 30, 2018, which claims the benefit of the filing date to U.S. Provisional Application No. 62/457,627, filed on 10 Feb. 2017, the entire disclosures of which are incorporated by reference herein.

BACKGROUND

1. Field of the Invention

The present invention is generally related to electrodes for electrochemical sensors, such as for biosensors. More particularly, the present invention is related to electrodes comprising a palladium metal layer and a palladium oxide-containing layer.

2. Description of the Related Art

Biosensors for use in analyzing biological samples are becoming increasingly prevalent. For example, with the rise in cases of diabetes in the world's population, the need for biosensors for measuring blood glucose has risen dramatically. Such biosensors are generally known as glucometers and operate by having a user place a drop of blood on a test-strip associated with the glucometer. The test-strip is configured to be reactive to the amount of glucose in the drop of blood, such that the glucometer can detect and display a glucose level of the user's blood.

The test-strips for glucometer-type biosensors are generally formed with two or more electrodes (e.g., a working electrode and a counter electrode) formed on a substrate. In addition, a bio-reactant that reacts with a biological sample, e.g., an enzyme (e.g., glucose oxidase, glucose dehydrogenase, or the like), and a mediator (e.g., ferricyanide, ruthenium complexes, osmium complexes, quinones, phenothiazines, phenoxazines, or the like) are formed on at least one of the electrodes, e.g., the working electrode. In operation, a drop of blood will be applied to a test-strip. Thereafter, an electrochemical reaction proportional to the amount of glucose in the blood will take place on the working electrode. In more detail, glucose first reacts with the bio-reactant, e.g., enzyme (glucose oxidase, glucose dehyrogenase, or the like) and sometimes an enzyme cofactor (PQQ, FAD, or the like) and is oxidized to gluconic acid. The bio-reactant, e.g., enzyme, cofactor, or enzyme-cofactor complex, is temporarily reduced by two electrons transferred from glucose to the enzyme, cofactor, or enzyme-cofactor complex. Next, the reduced enzyme, cofactor, or enzyme-cofactor complex reacts with the mediator, transferring a single electron to each of two mediator species (molecules or complexes), in the case of a mediator that is reduced in a one-electron process. When the mediator species are reduced, the enzyme, cofactor, or enzyme-cofactor complex is thus returned to its original oxidation state. Then, the reduced mediators diffuse to the electrode surface where a pre-determined and sufficiently oxidizing potential is applied to the biosensor so that the reduced mediators are oxidized back to their original oxidation state. The current that is generated by the oxidation of the mediator species by the biosensor is measured and related proportionally to the amount of glucose in the blood.

The quality of the working electrode plays an important role in an accurate measurement of the glucose level of the blood. Specifically, each of (1) the reproducibility of the electroactive surface area of the electrode, (2) the lot-to-lot repeatability of the electron transfer kinetics of the electrode in a particular glucose measurement arrangement, and (3) the long-term stability of the electrode material while in storage, are all factors that lead to improved accuracy of blood glucose test strips.

Many metal-based electrode compositions are somewhat unstable because they are susceptible to atmospheric aging. Such aging of the electrodes, which results from exposure to the environment, can vary the electrodes' physical and chemical characteristic. As such, the electrodes may experience a reduction in electrochemical performance and accuracy.

To alleviate such aging issues, many commercial biosensors use electrode materials that are intrinsically noble, such as gold, palladium, platinum, iridium, and the like. Such noble metals are generally considered to be minimally reactive with interfering substances (e.g., the atmosphere), and as a result, are thought to offer enhanced chemical resistance for consistent and accurate measurements. However, it has been found that even noble metals, such as palladium, do experience atmospheric aging and, thus, do experience physical and chemical changes over time.

Accordingly, there is a need for an electrode for electrochemical sensors, such as biosensors, that provides consistent and accurate measurements throughout the usable life of the sensors. In particular, there is a need for an electrode that can withstand the negative effects of atmospheric aging but that does not experience significant reduction in the conductivity of the electrode and/or does not experience a significant change in the heterogeneous electron transfer kinetics when used with common redox mediators.

SUMMARY

One or more embodiments of the present invention concern an electrochemical electrode for use in a biosensor. The electrode comprises a substrate, a palladium metal layer manufactured on the substrate, and a palladium oxide-containing layer manufactured on the palladium metal layer. The palladium metal layer has a thickness of no more than 90 nm, and the palladium oxide-containing layer has a thickness of no more than 40 nm.

One or more additional embodiments of the present invention concern an electrochemical electrode for use in a biosensor. The electrode comprises a substrate, a palladium metal layer manufactured on the substrate, and a palladium oxide-containing layer manufactured on the palladium metal layer. A ratio of a thickness of the palladium oxide-containing layer to a thickness of the palladium metal layer is no more than 3:5.

One or more additional embodiments of the present invention concern a method for producing an electrochemical electrode for a biosensor. The method comprises an initial step of providing a substrate. An additional step includes sputtering a palladium metal layer on the substrate in a first atmosphere consisting essentially of an inert gas. An additional step includes sputtering a palladium oxide-containing layer on the palladium metal layer in a second atmosphere comprising a mixture of the inert gas and an oxidant, with the oxidant making up between 0.5 and 40% of the second atmosphere by partial pressure.

One or more additional embodiments of the present invention concern an electrochemical electrode for use in a biosensor. The electrode comprises a substrate, a palladium metal layer formed on the substrate, and a palladium oxide-containing layer formed on the palladium metal layer. The electrode is configured to receive a particular fractional surface coverage (fractional coverage A) of Mercaptoethanesulphonate (MESA) on an outer surface of the electrode upon the electrode being coated with MESA, via a MESA Coating Procedure, within 10 days of the palladium metal layer and the palladium oxide-containing layer being formed. The electrode is configured to receive a separate fractional surface coverage (fractional coverage B) of MESA on the outer surface of the electrode upon the electrode being coated with MESA, via the MESA Coating Procedure, between 10 and 90 days after the palladium metal layer and the palladium oxide-containing layer being formed. The fractional coverage A deviates by no more than 30% from the fractional coverage B.

One or more additional embodiments of the present invention concern an electrochemical electrode for use in a biosensor. The electrochemical electrode comprises a substrate, a palladium metal layer formed on the substrate, and a palladium oxide-containing layer deposited on the palladium metal layer. Upon the electrochemical electrode being coated with Mercaptoethanesulphonate (MESA), via a MESA Coating Procedure, the electrochemical electrode is configured to receive a particular fractional surface coverage of MESA on an outer surface of the electrode. Upon a Baseline Electrode being immersed in MESA, via the MESA Coating Procedure, the Baseline Electrode is configured to receive a baseline fractional surface coverage of MESA on an outer surface of the Baseline Electrode. The electrochemical electrode is configured such that the particular fractional surface coverage of MESA on the electrochemical electrode deviates no more than 25% higher and/or 50% lower from the baseline fractional surface coverage of MESA on the Baseline Electrode when the electrochemical electrode receives the particular fractional coverage of MESA within 10 days of the palladium metal layer and the palladium oxide-containing layer being formed.

One or more additional embodiments of the present invention concern an electrochemical electrode for use in a biosensor. The electrochemical electrode comprises a substrate, a palladium metal layer formed on the substrate, and a palladium oxide-containing layer formed on the palladium metal layer. The electrochemical electrode is configured to have a reduction peak, as determined by a Type 1 Cyclic Voltammetry Test, that is at least 10 mV more cathodic than a reduction peak, as determined by the Type 1 Cyclic Voltammetry Test, for a Baseline Electrode.

BRIEF DESCRIPTION OF THE FIGURES

Embodiments of the present invention are described herein with reference to the following figures, wherein:

FIG. 1 is a sectional schematic illustration of an electrode according to embodiments of the present invention, particularly illustrating a conductive film on a substrate;

FIG. 2 is a further detailed sectional schematic illustration of the electrode of FIG. 1, particularly illustrating the conductive film comprising a conductive layer and a oxide-containing layer;

FIG. 3 is a schematic illustration of a test-strip biosensor including an electrode according to embodiments of the present invention;

DETAILED DESCRIPTION

Figure 4:
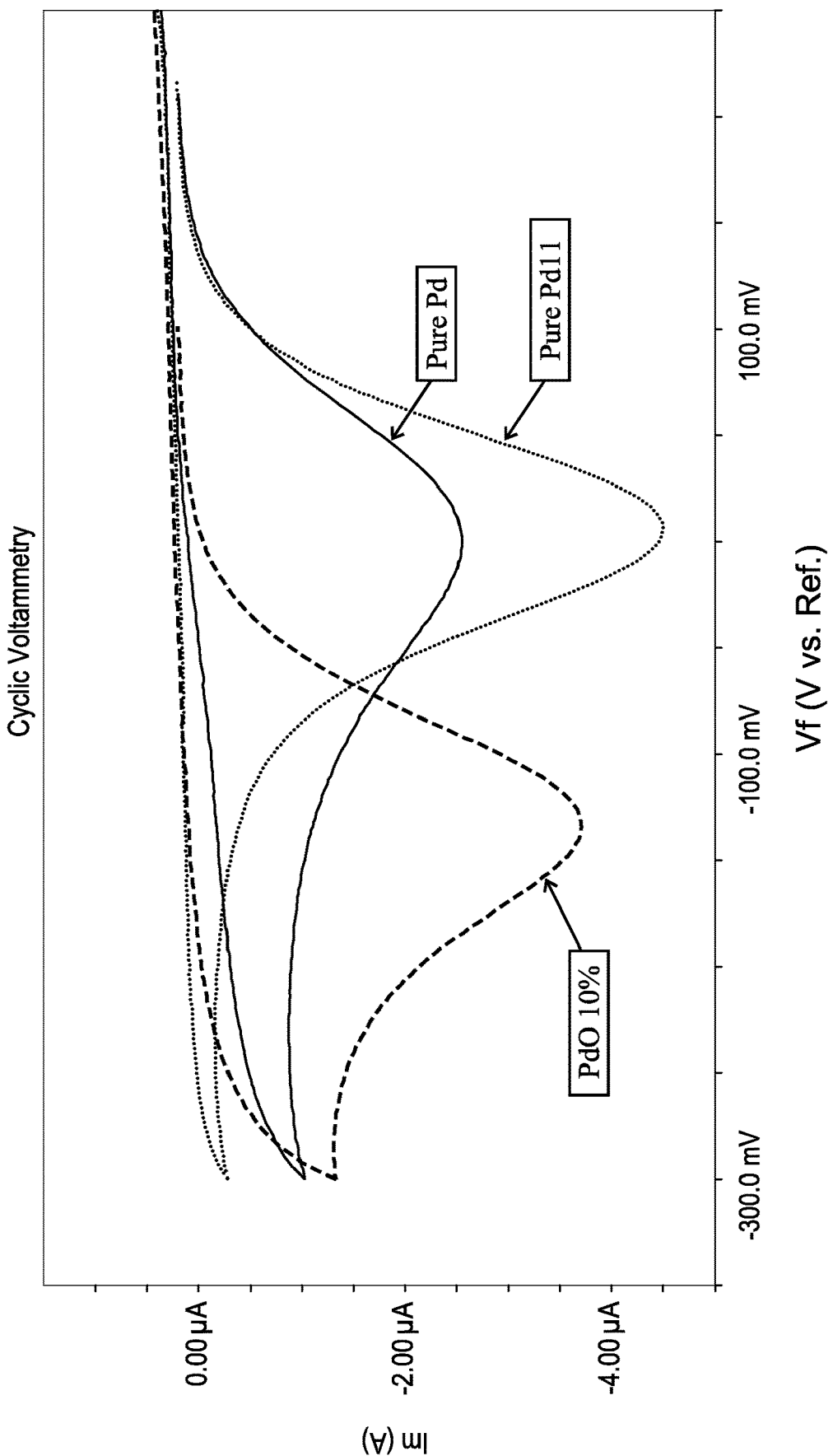
FIG. 4 is a graph depicting a polarization scan of three electrodes having undergone a Type 1 Cyclic Voltammetry Test.

The present invention is broadly directed to a composition of an electrode for an electrochemical sensor, such as a biosensor. As used herein, the term "biosensor" shall denote a device for analyzing biological samples. In some embodiments, as illustrated in FIG. 1, the electrode may be a layered thin-film electrode (electrode 100) and may broadly comprise a substrate 102 and a conductive film 104 coated on at least a portion of the substrate 102. As shown in FIG. 2, the conductive film 104 may comprise a conductive layer 106 and an oxide-containing layer 108. In such embodiments, the conductive layer 106 may be formed on the substrate 102, and the oxide-containing layer 108 may be formed on the conductive layer 106. Although the conductive film 104 includes the oxide-containing layer 106, the electrode 100 formed according to embodiments of the present invention provides for the conductive film 104 to have sufficient conductivity and electrochemical response for use in an electrochemical sensor.

As noted above, in some embodiments, the electrode 100 may be used in a biosensor. The biosensor may be a medical sensor, such as a blood glucose sensor or a glucometer. As used herein, the term "medical sensor" shall denote a biosensor used for medical monitoring and/or diagnosis. Additionally, the term "blood glucose sensor" shall denote a medical sensor used to determine a concentration of glucose in blood. As such, the electrode 100 described herein may form part of a test-strip used in a medical sensor, such as blood glucose sensor. For instance, as illustrated in FIG. 3, some embodiments contemplate that the medical sensor may comprise a test-strip 110 that includes a first electrode 100 separated from a second electrode 100 by a reaction space 112. The first electrode 100 may comprise a working electrode and the second electrode 100 may comprise a reference electrode or a counter electrode or a combined reference and counter electrode. As such, a biological sample, such as a drop of blood, can be placed within the reaction space 112 and in electrical contact with the first and second electrodes 100 for analysis.

Unlike conventional biosensor electrodes, which normally include and/or use only a conductive film formed essentially of a noble metal, such as palladium and/or gold, the electrode 100 described herein can be formed to include a conductive film 104 comprising a conductive layer 106 formed from a noble metal, such as palladium, and an oxide-containing layer 108, which may be formed as layer containing an oxide of the same noble metal, such as palladium oxide. Although the electrode 100 includes an oxide-containing layer 108, the combination of the conductive layer 106 and the oxide-containing layer 108 described herein is configured to provide superior consistency and accuracy when measuring biological samples, while simultaneously withstanding atmospheric aging.

In more detail, embodiments of the present invention provide for the substrate 102 of the electrode 100 to be formed from any type of material, either flexible or rigid, that is generally non-conductive and chemically inert to the contemplated chemical reactions described herein. In certain embodiments, the substrate 102 may comprise a flexible, non-conductive film, including polymers, such as a polymeric film, a polyester film, a polycarbonate film, or the like. In certain specific embodiments, the substrate 102 may comprise a polyethylene terephthalate (PET) film. Embodiments of the present invention contemplate that the substrate 102 may have a thickness of at least 25 μm, 125 μm, or 250 μm, and/or not more than 800 μm, 500 μm, or 400 μm. In certain embodiments, the substrate 102 may have a thickness of between 25 to 800 μm, 25 to 500 μm, or 25 to 400 μm, between 125 to 800 μm, 125 to 500 μm, or 125 to 400 μm, or between 250 to 800 μm, 250 to 500 μm, or 250 to 400 μm.

As noted above, the conductive film 104 coated on the substrate 102 may comprise a conductive layer 106 and an oxide-containing layer 108. In some embodiments, the conductive layer 106 may consist essentially of palladium, and the oxide-containing layer 108 may comprise palladium oxide. Nevertheless, in other embodiments, the conductive layer 106 may comprise other metals (e.g., gold) or non-metals, and the oxide-containing layer 108 may comprise oxides of such other metals or may comprise oxides of other materials. The conductive layer 106 and the oxide-containing layer 108 may be manufactured on the substrate 102 via one or more physical vapor deposition techniques, such as sputter coating (e.g., magnetron sputtering, unbalanced magnetron sputtering, facing targets sputtering, or the like), thermal evaporation, electron beam evaporation, arc vaporization, co-evaporation, ion plating, or the like. Specifically, the conductive layer 106 may be manufactured on the substrate 102 (e.g., via sputtering), and the oxide-containing layer 108 may be manufactured on the conductive layer 106 (e.g., via sputtering). As used herein, the term "manufactured" is used to mean "intentionally fabricated." As such, when the oxide-containing layer 108 is described as being manufactured, such a description precludes the formation of an oxide-containing layer that naturally occurs, such as when the electrode is exposed to an ambient environment (e.g., an atmospherically-generated oxide-containing layer that naturally forms on the surface of a metal electrode that has been aged in an ambient environment).

The conductive film 104 may be formed on the substrate 102 to a thickness of at least 5, 10, 20, or 30 nm, and/or not more than 110, 100, 90, or 80 nm. In certain embodiments, the conductive film 104 may have a thickness of between 5 to 110 nm, 5 to 100 nm, 5 to 90 nm, 5 to 80 nm, between 10 to 110 nm, 10 to 100 nm, 10 to 90 nm, or 10 to 80 nm, between 20 to 110 nm, 20 to 100 nm, 20 to 90 nm, or 20 to 80 nm, or between 30 to 110 nm, 30 to 100 nm, 30 to 90 nm, or 30 to 80 nm.

As noted above, the conductive film 104 may be a multilayer film comprising the conductive layer 106 and the oxide-containing layer 108. As such, some embodiments of the present invention provide for the conductive layer 106 to be formed on the substrate 102 to a thickness of at least 0.5, 1, 2, 3 nm or 4 nm, and/or not more than 90, 80, 40, 10, or 5 nm. In certain embodiments, the conductive layer 106 may have a thickness of between 0.5 to 90 nm, 0.5 to 80 nm, 0.5 to 40 nm, 0.5 to 10 nm, or 0.5 to 5 nm, between 1 to 90 nm, 1 to 80 nm, 1 to 40 nm, 1 to 10 nm, or 1 to 5 nm, between 2 to 90 nm, 2 to 80 nm, 2 to 40 nm, 2 to 10 nm, or 2 to 5 nm, between 3 to 90 nm, 3 to 80 nm, 3 to 40 nm, 3 to 10 nm, or 3 to 5 nm, or between 4 to 90 nm, 4 to 80 nm, 4 to 40 nm, 4 to 10 nm, or 4 to 5 nm. In other embodiments, the conductive layer 106 may have a thickness of between 15 to 35 nm, between 20 to 30 nm, or about 25 nm.

In addition, the oxide-containing layer 108 of the conductive film 104 may be formed on the conductive layer 106 to a thickness of at least 0.5, 1, 2, or 3 nm, and/or not more than 20, 15, 10, or 5 nm. In certain embodiments, the oxide-containing layer 108 may have a thickness of between 0.5 to 20 nm, 0.5 to 15 nm, 0.5 to 10 nm, or 0.5 to 5 nm, between 1 to 20 nm, 1 to 15 nm, 1 to 10 nm, or 1 to 5 nm, between 2 to 20 nm, 2 to 15 nm, 2 to 10 nm, or 2 to 5 nm, or between 3 to 20 nm, 3 to 15 nm, 3 to 10 nm, or 3 to 5 nm. In other embodiments, the conductive layer 106 may have a thickness of between 5 to 15 nm, between 7 to 12 nm, or about 10 nm.

As such, embodiments may provide for the oxide-containing layer 108 to have a thickness that is not more than 70%, 60%, 50%, 40%, 30%, 20%, 10%, 5%, 4%, or 2% of a thickness of the conductive layer 106. Similarly, a ratio of the thickness of the oxide-containing layer 108 to the thickness of the conductive layer 106 may be no more than 7:10, 3:5, 1:2, 2:5, 1:3, 1:5, 1:10, 1:20, 1:25, or 1:50.

Although the conductive film 104 may include individual, discrete layers, in the form of the conductive layer 106 and the oxide-containing layer 108, in some embodiments, the individual layers may not be delineated from each other by a clear boundary. For instance, in some embodiments, the conductive layer 106 and the oxide-containing layer 108 may be connected by a connecting portion of material that includes an oxide transition gradient from the conductive layer 106 to the oxide-containing layer 108. As such, the connecting portion may be comprised essentially of conductive material (e.g., palladium) at locations close to the conductive layer 106 and may comprise higher amounts of oxide (e.g., palladium oxide) as the connecting portion transitions away from the conductive layer 106 to locations closer to the oxide-containing layer 108.

The conductive film 104 may be formed on the substrate 102, such that the resulting electrode 100 may have a sheet resistance, as measured by ASTM F1711-96, of at least 0.1, 0.5, 1, 5, or 10 ohms per square and/or no more than 200, 100, 50, 35, or 15 ohms per square. In some embodiments, the resulting electrode 100 may have a sheet resistance of between 0.1 to 200 ohms per square, 0.5 to 100 ohms per square, 1 to 50 ohms per square, 5 to 35 ohms per square, or 10 to 15 ohms per square.

Embodiments of the present invention provide for the conductive layer 106 of the conductive film 104 to be comprised essentially of a metal. In some embodiments, the metal of the conductive layer 106 may be a noble metal, such as palladium. As one skilled in the art would readily appreciate, although the conductive layer 106 may be comprised essentially of palladium, the conductive layer 106 may comprise incidental impurities. As used herein, "incidental impurities" refer to any impurities that naturally occur in the ore used to the produce the metal or that are inadvertently added during the production process. The conductive layer 106 may, in some embodiments, comprise less than about 0.1, 0.05, or 0.001 weight percent of the incidental impurities.

The oxide-containing layer 108 may comprise material containing an oxide of the metal forming the conductive layer 106. As such, for example, the oxide-containing layer 108 may comprise palladium oxide. The amount of oxide in the oxide-containing layer 108 may vary. For example, in some embodiments, the amount of oxide in the oxide-containing layer 108 may be at least 40%, at least 50%, at least 60%, at least 70%, at least 80%, at least 90%, at least 95%, or at least 99% of the oxide-containing layer 108 by weight. In addition, the amount of oxide in the oxide-containing layer 108 may be between 40 to 99%, 60 to 95%, or 80 and 90% by weight.

To form the electrode 100, embodiments of the present invention broadly provide for the conductive layer 106 and the oxide-containing layer 108 to be formed on the substrate 102, via physical vapor deposition, by performing the following steps:

(a) providing a substrate;
(b) providing a target;
(c) depositing material from the target onto the substrate in an inert atmosphere to thereby form a conductive layer on the substrate, with the conductive layer comprised essentially of material from the target; and
(d) depositing material from the target onto the conductive layer in an oxidant-containing atmosphere to thereby form a oxide-containing layer on the conductive layer, with the oxide-containing layer comprising an oxide of the material from the target.

The providing a substrate of step (a) may include the provision of any type of substrate material, such as PET, as was previously described. In certain embodiments, the substrate will comprise a sheet of substrate material that can be positioned within a high-vacuum chamber. The sheet of substrate material may comprise a single section of material, such as a square sheet. In some other embodiments, sheet of substrate material may comprise a roll of material that is passed, via a roll-to-roll mechanism, through the high vacuum chamber, as will be described in more detail below. In some embodiments, the substrate may be held stationary, while in other embodiments, the substrate may be rotated during deposition.

The providing a target of step (b) may include the provision of a physical vapor deposition target, which may comprise any of the conductive substances previously described. The target may be provided within the vacuum chamber in which the substrate is also provided. In some specific embodiments, the target may be comprised essentially of palladium. Such a target may comprise less than about 0.1, 0.05, or 0.001 weight percent of incidental impurities. In some embodiments, the target will be housed within and/or will comprise an electrode, such as a sputter cathode, during the physical vapor deposition process. In certain embodiments, the target may be a circular, tubular, rectangular, or the like. It should be understood, however, that embodiments of the present invention contemplate the use of other-shaped targets, with such targets having various sizes as may be necessary.

The depositing of step (c) generally includes the forming on the substrate of material from the target in an inert atmosphere to form the conductive layer. Similarly, the depositing of step (d) generally includes the forming on the conductive layer material from the target in an oxidant-containing atmosphere to form the oxide-containing layer.

As used herein, the term "physical vapor deposition" shall denote depositing thin-films by providing for the condensation of vaporized material onto a surface (e.g., the substrate). The physical vapor deposited coating may be performed with any type of physical vapor deposition process, e.g., sputter coating, thermal evaporation, electron beam evaporation, arc vaporization, co-evaporation, ion plating, or the like. For example, in some embodiments, the physical vapor depositing steps will be performed via a sputtering process, in which the substrate is coated with the conductive layer and the conductive layer is coated with the oxide-containing layer by sputtering the target, in an inert atmosphere and in an oxidant-containing atmosphere, respectively, via a sputtering device. Although the oxide-containing layer 108 of the electrode 100 may be manufactured by physical vapor deposition (e.g., sputtering), embodiments may provide for the oxide-containing layer 108 to be manufactured by other processes, such as corona treatments, oxygen plasmas, chemical oxidation, ion-assisted oxidation, or the like. As such, when the oxide-containing layer 108 is described herein as being "manufactured," such manufacturing may be performed via such above-described processes and procedures (e.g., sputtering, corona treatments, oxygen plasmas, chemical oxidation, ion-assisted oxidation, or the like).

In some embodiments, the depositing of steps (c) and (d) may be performed in a single-zone vacuum chamber. For example, for the depositing of step (c), a vacuum chamber may initially be brought to a vacuum and filled with a noble gas, such as argon, such that the conductive layer can be deposited on the substrate by sputtering the palladium target. In some embodiments, the depositing of step (c) may be performed by the sputtering system operating at a power of between 2 and 70 kW, between 7 and 35 kW, or about 8 kW. Next, the depositing of step (d) may be performed in the same vacuum chamber, after an oxidant has been added into chamber to create a noble gas and oxidant mixture, such that the oxide-containing layer can be deposited on the conductive layer. The oxidant used may vary, but may include oxygen, water, ozone, or the like. In certain embodiments, the oxidant may comprise between 0.5 and 40%, between 1 and 20%, between 2 and 10%, between 4 and 6%, or about 5% of the second atmosphere by partial pressure. The amount of oxide included in the electrode has shown to be controllable by controlling the amount of oxidant in the noble gas and oxidant mixture. It has also been determined that the oxide amount included in the electrode can be controlled by controlling the amount of time used to deposit the oxide-containing layer during the depositing of step (d). In some embodiments, the depositing of step (d) may be performed by the sputtering system operating at a power of between 2 and 70 kW, between 7 and 35 kW, or about 8 kW. Certain embodiments may provide for a ratio of the sputtering power used during said sputtering of step (c) (i.e., to deposit the conductive layer) and said sputtering of step (d) (i.e., to deposit the oxide-containing layer) to be about 2:1, about 3:1, about 4:1, about 5:1, about 6:1, about 7:1, about 8:1, about 9:1, or about 10:1.

Instead of a single-zone vacuum chamber, in some embodiments, the depositing of steps (c) and (d) may be performed in at least two different zones of a vacuum chamber (e.g., a dual-zone vacuum chamber). For example, such embodiments may be performed by roll-to-roll physical vapor deposition process that includes roll-to-roll magnetron sputtering. Initially, the substrate may be provided to a first vacuum chamber zone that includes a first target positioned therein. For the depositing of step (c), the first vacuum chamber zone may be filled with a noble gas, such as argon, such that the conductive layer can be deposited on the substrate by sputtering the substrate with material from the first target within the first chamber zone. Thereafter, the substrate coated with the conductive layer deposited thereon may be transferred to a second vacuum chamber zone with a second target positioned therein. In some embodiments, the first and second targets may be the same material. Next, the depositing of step (d) may be performed in the second vacuum chamber zone, which is filled with a mixture of noble gas and an oxidant, such that the oxide-containing layer can be deposited on the conductive layer.

Regardless of whether a single-zone vacuum chamber or a dual-zone vacuum chamber is used, the resulting substrate with the conductive layer and the oxide-containing layer formed thereon may be prepared in thin-film sheets, which may be cut to size and used as electrochemical electrodes, such as for biosensors. Such electrodes may include a working electrode, a reference electrode, or a counter electrode. Specifically, the resulting thin-film sheets may be cut apart to appropriate size to form an electrochemical electrode specifically sized for the biosensor. In other embodiments, the electrochemical electrodes can be formed from the thin-film sheet by etching, such as chemical or laser etching (or ablation). In still other embodiments, electrochemical electrodes can be formed using a patterned mask, which is laid on the substrate, and the conductive layer and oxide-containing layer are physical vapor deposited there over to form the electrode.

As previously noted above, an electrode formed according to embodiments of the present invention, which includes a conductive layer formed as a palladium metal layer and an oxide-containing layer formed as a palladium oxide-containing layer, can exhibit desirable electrochemical properties and can withstand the effects of atmospheric aging. As such, the electrodes of embodiments of the present invention are particularly well suited as replacements for biosensor that incorporate pure noble metals, such as palladium and/or gold. Specifically, it has been found that the palladium oxide-containing layer formed on the palladium metal layer can restrict additional oxidation and surface modification of the electrode, such that the electrode can be formed to reduce or minimize the effects of atmospheric aging (e.g., further oxidation). The degree to which the electrode can withstand atmospheric aging has been found to be related to the amount of palladium oxide formed on the surface of the electrode. For example, electrodes with a higher oxide surface coverage are more resistant to atmospheric aging than electrodes with lower oxide surface coverage. However, it should be understood that the there is a maximum beneficial amount of oxide surface coverage for an electrode, as too much oxide in an electrode can reduce the conductivity of the electrode below an operable level. Embodiments of the present invention control the amount of palladium oxide on the surface of the electrode by controlling the amount of oxidant added to the deposition atmosphere during deposition of the palladium oxide-containing layer and/or by controlling the deposition time used to deposit the palladium oxide-containing layer. In other embodiments, which incorporate other processes for forming the palladium oxide-containing layer (e.g., corona treatments, oxygen plasmas, chemical oxidation, ion-assisted oxidation, or the like), the amount of palladium oxide in the electrode may be controlled by controlling various parameters (e.g., treatment time) of such other processes.

In view of the above, it has been determined that the stability (i.e., the ability to withstand the effects of atmospheric aging) of an electrode formed according to embodiments of the present invention can be quantified by the amount of oxide formed on the surface of the electrode. For palladium-based electrodes, an amount of palladium oxide on the surface of the electrode can be determined by measuring the amount of and/or the rate at which Mercaptoethanesulphonate (MESA) is retained on the surface of the electrode after the electrode is coated with MESA. In particular, it has been determined that the rate at which MESA adheres to an electrode's surface decreases with the oxide surface coverage of the electrode. Thus, a palladium electrode with a high amount of palladium oxide on its surface will allow a lower amount of MESA to adhere to the electrode surface upon being coated with MESA over a given coating period. Contrastingly, a palladium electrode with a low amount of palladium oxide on its surface will allow a higher amount of MESA to adhere to the electrode upon being coated with MESA over the given time period. Thus, each of (1) the rate at which MESA is coated on an electrode (i.e., MESA kinetics), and (2) the surface coverage of MESA on an electrode after being coated in MESA for a given time period (i.e., MESA coverage), are both inversely proportional to the surface oxidation of the electrode.

For an electrode to be stable and to withstand the effects of atmospheric aging, the electrode should have an oxide surface coverage that is consistent over the life of the electrode. Such an electrode would have MESA kinetics that are consistent regardless of when the electrode is coated with MESA. On the other hand, an electrode that is not stable and is not capable of withstanding the effects of atmospheric aging will have its oxide surface coverage increase over the life of the electrode as the electrode is exposed to the atmosphere. As noted above, the MESA kinetics of an electrode is known to decrease with increasing oxide surface coverage of the electrode. As such, electrodes that are atmospherically unstable will have MESA kinetics that decline over the life of the electrodes. In contrast, electrodes that are atmospherically stable will have MESA kinetics that are generally stable over the life of the electrodes.

Electrodes formed according to embodiments of the present invention, i.e., with a palladium metal layer formed on a substrate and a palladium oxide-containing layer formed on the palladium metal layer, are shown to be atmospherically stable. For example, an electrode formed according to embodiments of the present invention may be configured to receive a particular fractional coverage (fractional coverage A) of MESA, as determined by the Type 1 MESA Coverage Test (as defined below), on an outer surface of the electrode upon the electrode being coated in MESA, via a MESA Coating Procedure (as defined below), within 10 days of the palladium layer and the palladium oxide-containing layer being formed. In addition, the electrode is configured to receive a separate fractional coverage (fractional coverage B) of MESA, as determined by the Type 1 MESA Coverage Test, on the outer surface of the electrode upon the electrode being coated in MESA, via the MESA Coating Procedure, between 10 and 90 days after the palladium metal layer and the palladium oxide-containing layer being formed. Embodiments of the present invention provide for the fractional coverage A to deviate by no more than 30%, 20%, 15%, 10%, 7%, 6%, 5%, 4%, 3, or 2% from the fractional coverage B.

In various embodiments, electrodes formed according to embodiments of the present invention when coated with MESA, via the MESA Coating Procedure, are configured to receive a particular fractional coverage of MESA, as determined by the Type 1 MESA Coverage Test, on an outer surface of the electrode. Contrastingly, upon a Baseline Electrode (which is defined herein as an electrode formed essentially of a palladium metal layer sputtered in an inert atmosphere to at least a thickness of 10 nm on a substrate and aged in an ambient atmosphere for at least 90 days) being coated in MESA, via the MESA Coating Procedure, the Baseline Electrode is configured to receive a baseline fractional coverage of MESA, as determined by the Type 1 MESA Coverage Test, on an outer surface of the Baseline Electrode. The electrode of the present invention is configured such that the particular fractional coverage of MESA on the electrode deviates no more than 25%, 20%, 15%, 10%, or 5% higher and/or 50%, 40%, 30%, 20%, or 10% lower than the baseline fractional coverage of MESA on the Baseline Electrode when the electrode of the present invention receives the particular fractional coverage of MESA within 10 days of the palladium metal layer and the palladium oxide-containing layer being formed.

Although it is beneficial that the electrodes formed according to embodiments of the present invention are atmospherically stable, such that they can withstand the effects of atmospheric aging, it is also important that the electrodes suitably perform electrochemically. As will be illustrated in the below examples, the electrodes formed according to embodiments of the present invention, i.e., with a palladium metal layer formed on a substrate and a palladium oxide-containing layer formed on the palladium metal layer, are shown to perform electrochemically similar to electrodes formed essentially of noble metals, such as pure palladium electrodes. Specifically, the electrodes formed according to embodiments of the present invention have similar heterogeneous electron transfer or conductivity as commonly-used electrodes (e.g., pure palladium electrodes). Nevertheless, although the electrodes perform electrochemically similar to other commonly-used electrodes, it has been found that the electrodes of the present invention have different oxide structures on their surfaces, such that reduction waves of the electrodes produce different signatures than reduction waves of commonly-used electrodes. For example, an electrode formed according to embodiments of the present invention is configured to have a reduction peak, as determined by a Type 1 Cyclic Voltammetry Test, that is at least 10 mV more cathodic than a reduction peak, as determined by the Type 1 Cyclic Voltammetry Test, for a Baseline Electrode.

This invention can be further illustrated by the following examples of embodiments thereof, although it will be understood that these examples are included merely for the purposes of illustration and are not intended to limit the scope of the invention unless otherwise specifically indicated.

EXAMPLES

Preparation of Thin-Film Electrodes

For each of the below-described examples, electrodes were formed by one of the following physical vapor deposition processes. As such, it is understood that the electrodes of embodiments of the present invention can be formed, using the below processes, to include a conductive layer of a palladium metal formed on a substrate, and an oxide-containing layer comprising palladium oxide formed on the conductive layer. A single-zone vacuum chamber process includes forming electrode thin-films sheets by performing the following steps:

(a) a palladium metal layer was deposited on a 10.16 cm×10.16 cm square PET substrate sheet using direct current ("DC") magnetron sputtering in a high vacuum chamber, with the sputtering having been performed with a Denton Vacuum Desktop Pro sputtering device—
  i. the vacuum chamber was evacuated to an initial base pressure of $\sim 10^{-5}$ mTorr;
  ii. argon gas of 10 sccm was introduced into the high vacuum chamber to create a deposition pressure of 5 mTorr;
  iii. the substrate sheet was rotated at approximately two revolutions per minute within the vacuum chamber;
  iv. a 5.08 cm diameter target of palladium was held at a constant power of 40 Watts under the DC magnetron sputtering device for deposition time of 4 minutes in the pure argon atmosphere to coat at least a portion of the substrate sheet with the conductive palladium metal layer (to initialize the targets, the targets were held at a constant power of 40 Watts under the DC magnetron sputtering device for a 5 minute pre-sputtering time prior to the substrates being introduced into the vacuum chamber);
(b) a palladium oxide-containing layer was deposited on the palladium metal layer via the sputtering device—
  i. an oxygen and argon gas mixture of 10 sccm was introduced into the high vacuum chamber to create a deposition pressure of 5 mTorr;
  ii. the substrate sheet was rotated at approximately two revolutions per minute within the vacuum chamber;
  iii. the palladium target was held at a constant power of 40 Watts under the DC magnetron sputtering device for deposition time of 1 minute in the oxygen and argon atmosphere to coat at least a portion of the palladium metal layer with a palladium oxide-containing layer; and
(c) all depositions were carried out at room temperature (i.e., 25° C.).

In addition to the single-zone vacuum chamber process, certain electrodes of embodiments of the present invention, which are described in the below examples, were formed via a dual-zone vacuum chamber process using roll-to-roll equipment. In more detail, the process for the dual-zone vacuum chamber is similar to that described above except two palladium targets were used, with one in each vacuum chamber zone. In addition, the first zone was pumped with pure argon to begin formation of the electrode thin-film sheet by depositing the palladium metal layer on the substrate. Thereafter the electrode thin-film sheet was transferred (roll-to-roll) to the second zone. Oxygen was supplied to the second zone to create an argon/oxygen mixture for deposition of the palladium oxide-containing layer on the palladium metal layer.

As such, electrode thin-film sheets comprising a palladium metal layer on a substrate and a palladium oxide-containing layer on the palladium metal layer were formed. Regardless of whether the single-zone or dual-zone vacuum chamber processes were used, individual electrodes, with a size of 5.08 cm×7.62 cm, were cut from the electrode thin-film sheets. As described in detail below, certain electrodes had their electrochemical properties tested via a potentiostat. In addition, some electrodes were tested after further undergoing a coating of 2-Mercaptoethanesulphonate ("MESA"), as described in more detail below.

Electrochemical experiments were conducted using a Gamry Instruments Reference 600 potentiostat in a three electrode configuration, with the electrochemical cell containing the thin-film electrode film positioned inside of a Gamry Instruments VistaShield Faraday Cage. Each of the thin-film electrodes was formed as a working electrode by partially masking the thin-film electrode with electroplating tape having a single 3 mm diameter aperture die-cut into it. As such, an unmasked portion of the thin-film electrode provided a geometric working electrode surface area of 0.0707 square cm. The unmasked portion of the thin-film electrode served as an electrical connection point to a working electrode lead of the potentiostat. The masked portion of the thin-film electrode was placed onto a flat supporting block of non-conductive material, such as plastic. The thin-film electrode was thereafter placed into a working electrode port of a glass electrochemical cell. The exposed 3 mm diameter portion of the thin-film electrode was positioned near a center of a bottom opening of working electrode port of the electrochemical cell. The working electrode port of the electrochemical cell was sealed with a clamp and an O-ring. The electrochemical cell also contained a reference electrode comprising a saturated calomel reference electrode and a carbon auxiliary electrode. The reference electrode and the auxiliary electrode were placed, respectively in a reference electrode port and an auxiliary electrode port. Additionally, the reference electrode and the auxiliary electrode were connected, respectively, to a reference lead and an auxiliary lead of the potentiostat. The electrochemical cell also included a gas flow port by which to deaerate and blanket test solutions with inert gas, such as nitrogen.

Description of Type 1 Cyclic Voltammetry Test

Certain of the examples to follow were performed using a Type 1 Cyclic Voltammetry Test, which is defined as follows: 50 mL of potassium phosphate buffer solution containing 145 mM sodium chloride at pH 7.1 ("PBS") was placed into the electrochemical cell and the electrochemical cell was sealed with stoppers. Alternatively, 50 mL of 0.1 M potassium chloride may be used for the PBS. Gas inlet and outlet fittings, which were associated with the gas flow port, allowed inert gas sparging (i.e., de-aerating) of the PBS, via a gas flow of nitrogen, using a medium-porous filter stick. The gas flow port additionally allowed the gas flow to be switched from the filter stick to a headspace-blanketing arrangement. The gas outlet was connected to an oil bubbler to prevent back-diffusion of external gas (e.g., air) into the electrochemical cell. The PBS was stirred with a magnetic stirbar while simultaneously sparged with nitrogen for at least 5 minutes before switching the gas flow to a blanketing configuration. No agitation of the solution (from sparging or otherwise) was present during the electrochemical experiments conducted, i.e., the PBS was quiescent during electrochemical testing.

Cyclic voltammetry was performed on the thin-film electrode that formed the working electrode within the electrochemical cell. The initial voltage potential for the Type 1 Cyclic Voltammetry was 0 V versus the open circuit (i.e., the rest potential), as measured between the working electrode and the reference electrode (i.e., the saturated calomel reference electrode) after a rest period of at least 10 seconds prior to the experiment. The voltage potential was swept, at a scan rate of 25 mV per second, cathodically first followed by an anodic potential sweep.

Description of Type 2 Cyclic Voltammetry Test

A Type 2 Cyclic Voltammetry Test was performed in the same manner as the Type 1 Cyclic Voltammetry Test except that the PBS was replaced with 50 mL of 0.1 M sodium hydroxide.

Description of Type 3 Cyclic Voltammetry Test

The experimental setup for the Type 3 Cyclic Voltammetry Test was similar to that of the Type 1 Cyclic Voltammetry Test except that 1 mM of Fe[III](CN)$_6$ was added to the PBS as a redox mediator. In addition, the procedure of the Type 3 Cyclic Voltammetry Test was as follows:

(1) The initial potential of the thin-film electrode was at 0 V versus the open circuit potential (i.e., the rest potential);
(2) The potential of the thin-film electrode is scanned cathodically at 25 mV per second to a potential of −0.3 V (versus the reference electrode); and
(3) The potential of the thin-film electrode is scanned anodically at 25 mV per second to a potential of approximately 1 V (versus the reference electrode).

Description of Type 4 Cyclic Voltammetry Test

The experimental setup of for the Type 4 Cyclic Voltammetry Test was similar to that of the Type 1 Cyclic Voltammetry Test except that the 2 mM of 3(2',5'-Disulfophenylimino)-3H-phenothiazine was added to the PBS.

Applications of Type 1 Cyclic Voltammetry Test

Experiment of FIG. 4

FIG. 4 illustrates the results of three electrodes that underwent a Type 1 Cyclic Voltammetry Test. Each of a first electrode (Pure Pd) and a second electrode (Pure Pd11) were formed by sputtering a palladium target in a pure argon atmosphere without the introduction of oxygen during the sputtering process. As such, the first electrode and a second electrode were formed essentially of a palladium metal layer on a substrate. The first electrode was not atmospherically aged and immediately underwent the Type 1 Cyclic Voltammetry Test. The second electrode was atmospherically aged for 11 months and then underwent the Type 1 Cyclic Voltammetry Test. FIG. 4 also illustrates a third electrode (PdO 10%), which is an electrode formed according to embodiments of the present invention. In particular, the third electrode was formed by sputtering a palladium target in a pure argon atmosphere for four minutes to create a palladium metal layer on the substrate. In addition, the third electrode was formed with a palladium oxide-containing layer on the palladium metal layer by sputtering the palladium target in an argon/oxygen atmosphere mixture containing 10% oxygen for 1 minute. It should be understood that in each of the examples described herein, the specific oxygen percentages stated are in partial pressures of the total argon/oxygen atmosphere pressure within the vacuum chamber. The third electrode was not atmospherically aged and immediately underwent the Type 1 Cyclic Voltammetry Test.

Because the second electrode was allowed to atmospherically age for 11 months, the second electrode reacted with the atmosphere to generate an atmospherically-generated palladium oxide layer on the outer surface of the palladium metal layer. Contrastingly, because the first electrode was not allowed to age, the first electrode did not include a palladium-oxide layer that included as much oxide as that of the second electrode, as is indicated in the electrochemical analysis illustrated in FIG. 4. As illustrated by FIG. 4, the reduction wave of the second electrode is significantly larger than that of the first electrode, thus, indicating that a palladium oxide layer on the surface of the palladium conductive layer alters the electrode's electrochemical response when undergoing the Type 1 Cyclic Voltammetry Test. Furthermore, the reduction wave of the third electrode was shown to be significantly larger than the first electrode, and furthermore, was found to have a peak that shifted significantly in a cathodic direction with respect to both the first electrode and the second electrode. It was unexpected that the reduction wave of the third electrode, with its palladium oxide-containing layer having been generated during the sputtering process, would have been significantly different (i.e., with a cathodically-shifted peak) than the reduction wave of the second electrode, with its palladium oxide-containing layer having been naturally generated during atmospheric aging. Such a difference is indicative of differing oxide structures on the surface of the respective electrodes.

Figure 5:
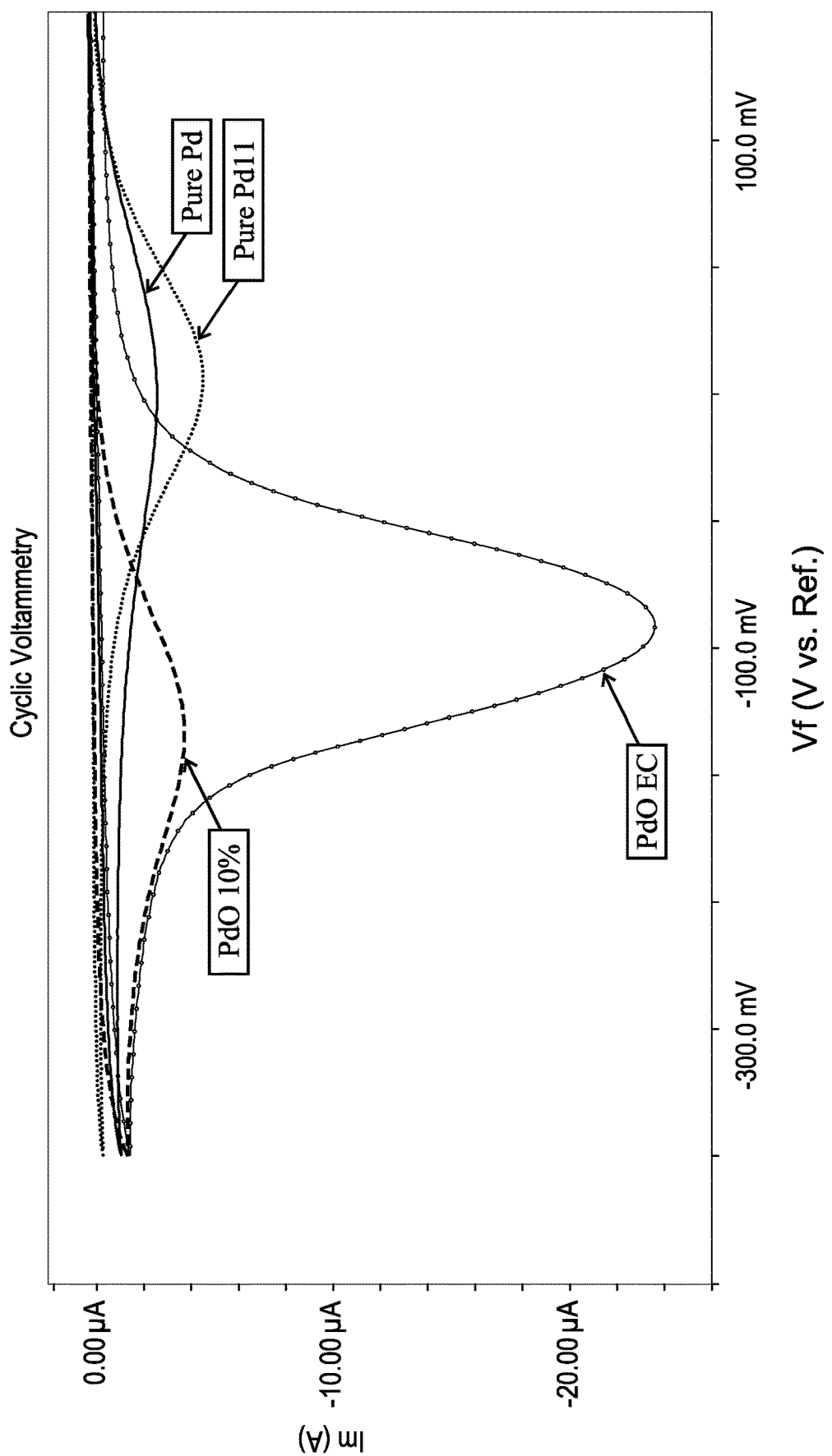
FIG. 5 is a graph depicting a polarization scan of four electrodes having undergone a Type 1 Cyclic Voltammetry Test.

Experiment of FIG. 5

FIG. 5 again illustrates the results of the three electrodes (i.e., Pure Pd, Pure Pd11, and PdO 10%) that underwent a Type 1 Cyclic Voltammetry Test, as previously illustrated in FIG. 4. In addition, FIG. 5 illustrates a fourth electrode (PdO EC) that underwent a Type 1 Cyclic Voltammetry Test. The fourth electrode was formed by sputtering a palladium target in a pure argon atmosphere without the introduction of oxygen during the sputtering process. As such, the fourth electrode was initially formed essentially of a palladium metal layer on a substrate. However, before undergoing the Type 1 Cyclic Voltammetry Test, the fourth electrode was first scanned anodically to 1.1 V, so as to electrochemically generate a palladium oxide-containing layer on the surface of the palladium metal layer.

As illustrated by FIG. 5, the reduction wave of the fourth electrode was significantly larger than that of each of the other electrodes. It was unexpected that the reduction wave of the third electrode (PdO 10%), with its palladium oxide-containing layer having been generated during the sputtering process, would have been significantly different than the signature of the reduction wave of the fourth electrode, with its palladium oxide-continuing layer having been electrochemically generated during anodic scanning. Such a difference is indicative of differing oxide structures on the surface of the respective electrodes.

Figure 6:
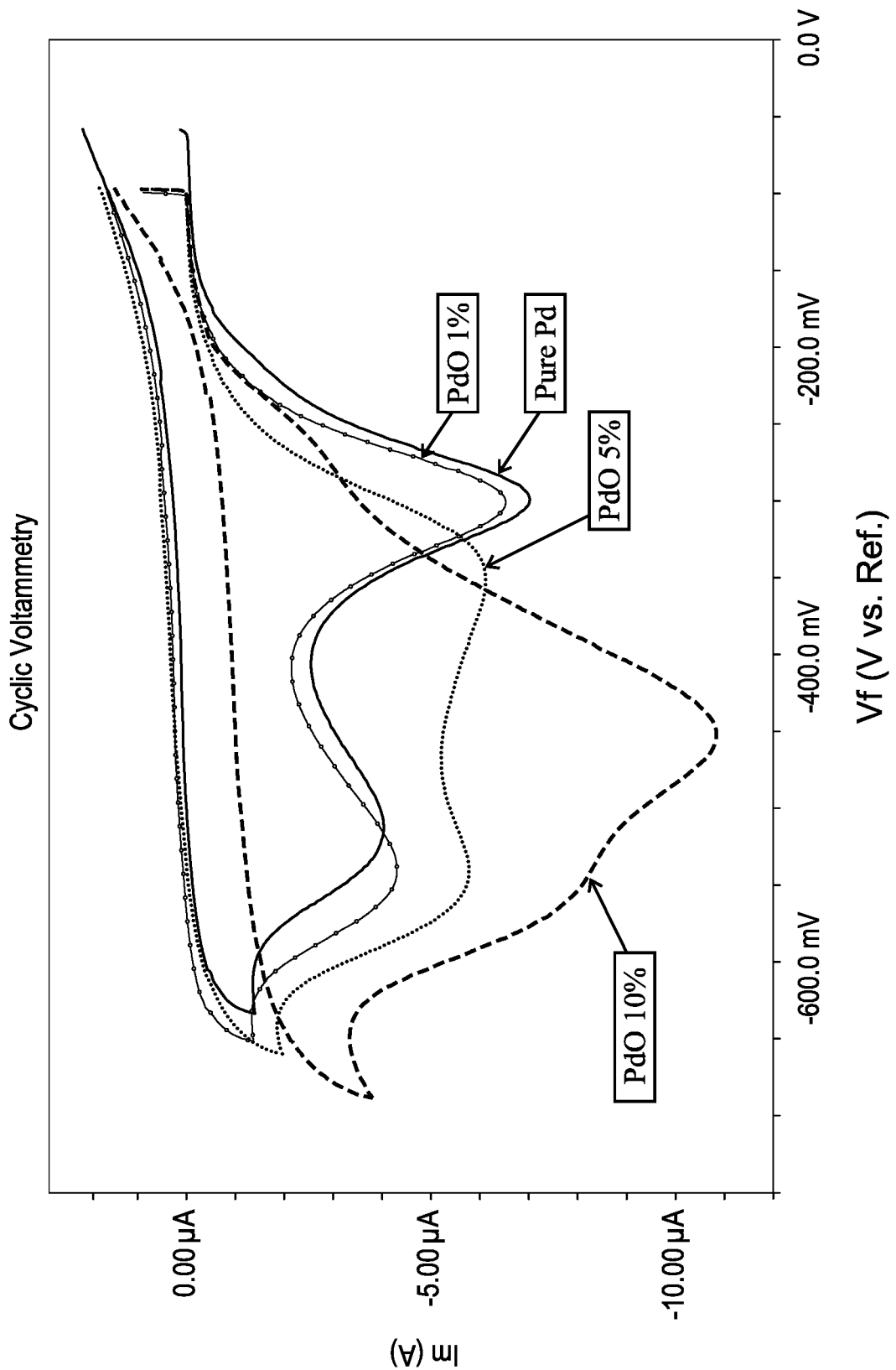
FIG. 6 is a graph depicting a polarization scan of four electrodes having undergone a Type 2 Cyclic Voltammetry Test.

Experiment of FIG. 6

FIG. 6 illustrates the results of four electrodes that underwent a Type 2 Cyclic Voltammetry Test. The first electrode (Pure Pd) was formed in a roll-to-roll deposition machine with a first zone and a second zone. The first electrode was passed through the first zone to deposit 80% of the electrode's conductive film thickness. Thereafter, the first electrode was passed through the second zone to deposit the remaining 20% of the electrode's conductive film thickness. Each of the first zone and the second zone was filled with an atmosphere comprised essentially of argon (i.e., an inert gas), such that the first electrode was formed by sputtering a palladium target in each of the first and second zones without the introduction of oxygen during the sputtering process. As such, the first electrode was formed essentially of a palladium metal layer on a substrate. The second electrode (PdO 1%), the third electrode (PdO 5%), and the fourth electrode (PdO 10%) are each electrodes formed according to embodiments of the present invention. Specifically, the second, third, and fourth electrodes were formed in a roll-to-roll deposition machine with a first zone providing a pure argon atmosphere, and a second zone providing a mixed atmosphere of argon/oxygen. As such, each of the second electrode, the third electrode, and the fourth electrode was passed through the first zone to deposit 80% of the electrode's conductive film thickness. Thereafter, each of the electrodes was passed through the second zone to deposit the remaining 20% of the electrode's conductive film thickness. In more detail, each of the second electrode, the third electrode, and the fourth electrode was formed by sputtering a palladium target in the first zone containing the pure argon atmosphere so as to deposit a palladium metal layer on a substrate. Each of the second electrode, the third electrode, and the fourth electrode was then formed with a palladium oxide-containing layer on the palladium metal layer by sputtering a palladium target in the second zone containing the atmosphere comprising the mixture of argon and oxygen. Specifically, the second electrode was sputtered in an argon/oxygen atmosphere containing 1% oxygen. The third electrode was sputtered in an argon/oxygen atmosphere containing 5% oxygen. The fourth electrode was sputtered in an argon/oxygen atmosphere containing 10% oxygen. Each of the electrodes was then atmospherically aged for sixty days before undergoing the Type 2 Cyclic Voltammetry Test.

FIG. 6 illustrates that the reduction waves are significantly different for the electrodes that were sputtered in argon/oxygen atmospheres with higher oxygen concentrations than for the electrodes that were sputtered in argon/oxygen atmospheres with lower or no oxygen concentrations. For instance, the second electrode (i.e., PdO 1%) has a reduction wave that is similar to the first electrode (i.e., Pure Pd). Contrastingly, the third electrode (i.e., PdO 5%) and the fourth electrode (i.e., PdO 10%) have reduction waves that are significantly larger, and with peaks shifted in a more cathodic direction, than the first electrode and the second electrode. Furthermore, as noted above, each of the electrodes were atmospherically aged for 60 days post sputtering. The results of FIG. 6 are unexpected because the reduction waves of the electrodes formed according to embodiments of the present invention (e.g., PdO 1%, PdO 5%, and PdO 10%), even after atmospheric aging, do not convert back to the electrochemical response of electrodes formed essentially of palladium metal layers (e.g., Pure Pd), which were also allowed to atmospherically age.

Figure 7:
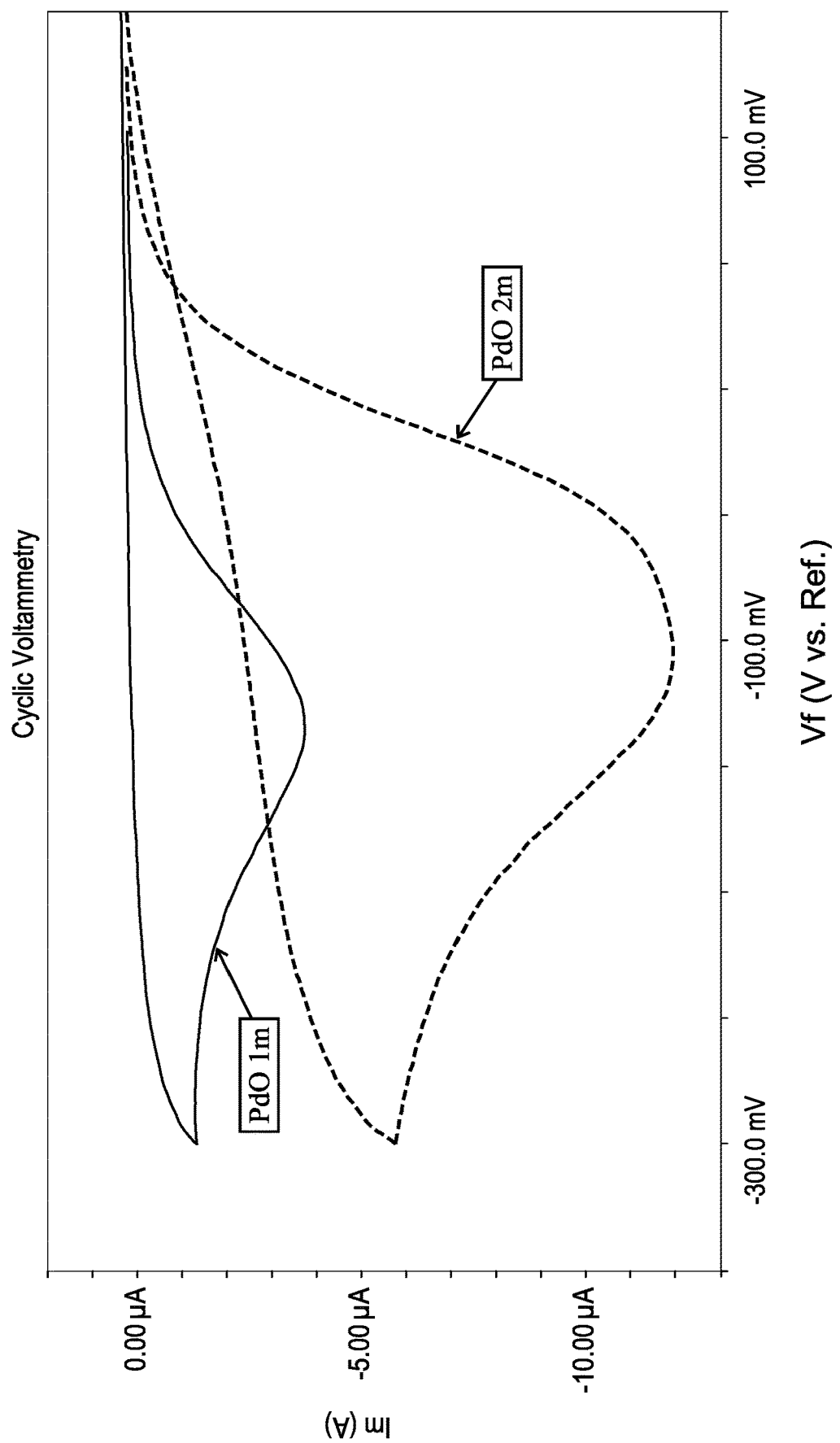
FIG. 7 is a graph depicting polarization scan of two electrodes having undergone a Type 1 Cyclic Voltammetry Test.

Experiment of FIG. 7

FIG. 7 illustrates the results of two electrodes that underwent a Type 1 Cyclic Voltammetry Test. The first electrode (PdO 1 m) and the second electrode (PdO 2 m) are each electrodes formed according to embodiments of the present invention. Specifically, the first electrode was formed by sputtering a palladium target in a pure argon atmosphere for four minutes to create a palladium metal layer on a substrate. Thereafter, the first electrode was then formed with a palladium oxide-containing layer on the palladium metal layer by sputtering the palladium target in an atmosphere containing an argon/oxygen mixture of 10% oxygen for one minute. The second electrode was formed by sputtering a palladium target in a pure argon atmosphere for three minutes to create a palladium metal layer on a substrate. Thereafter, the second electrode was formed with a palladium oxide-containing layer on the palladium metal layer by sputtering the palladium target in an atmosphere containing an argon/oxygen mixture of 10% oxygen for two minutes. Neither of the electrodes was allowed to significantly atmospherically age before undergoing the Type 1 Cyclic Voltammetry Test. FIG. 7 illustrates that the reduction waves of the electrodes are different, which is indicative of the surface structure of the palladium oxide-containing layers on the electrodes being different. Specifically, FIG. 7 illustrates that a thickness of the palladium oxide-containing layers on the electrodes can be controlled by the deposition time in the argon/oxygen atmosphere.

Figure 8:
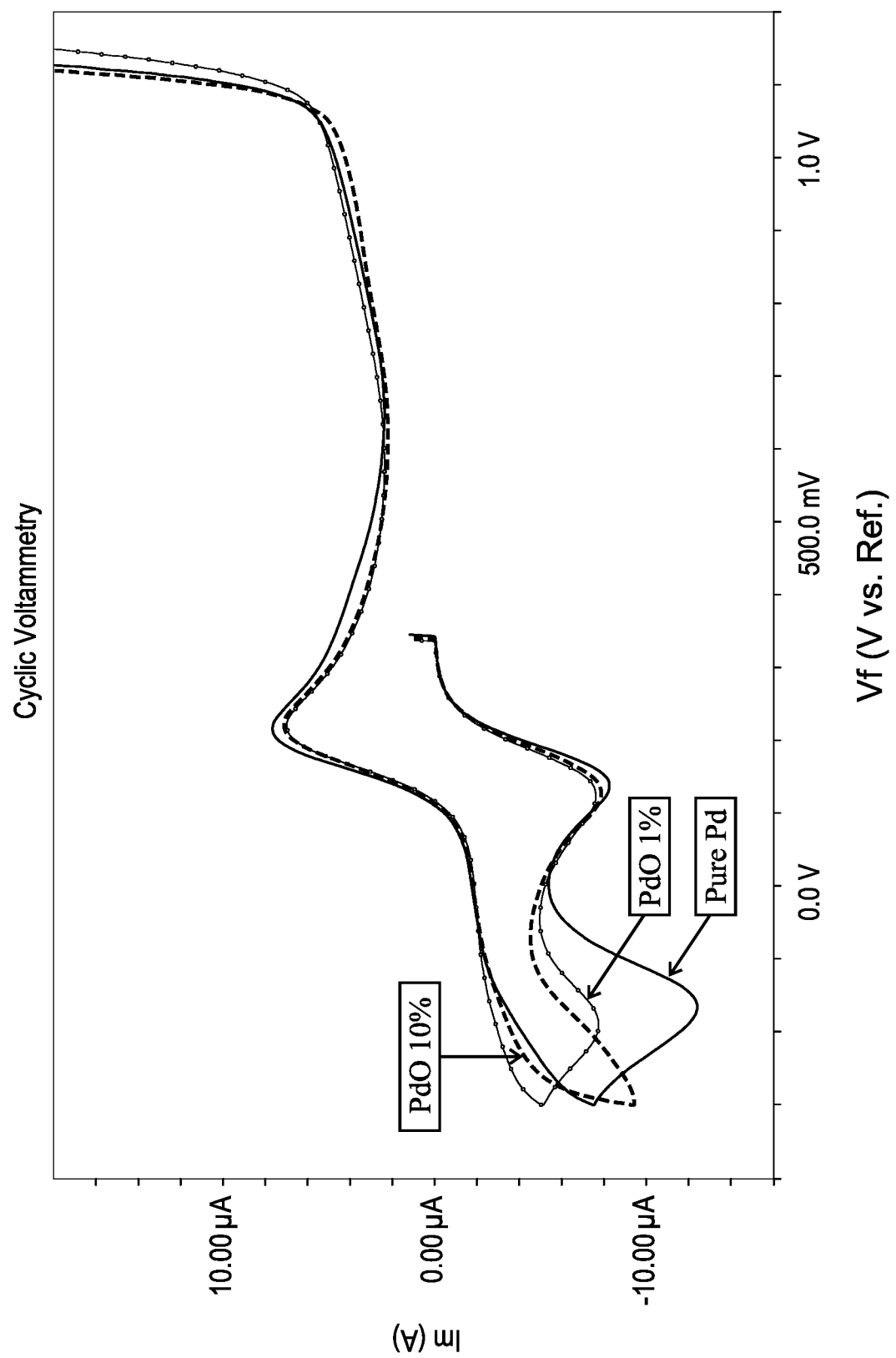
FIG. 8 is a is a graph depicting a cyclic voltammogram of three electrodes having undergone a Type 3 Cyclic Voltammetry Test.

Experiment of FIG. 8

FIG. 8 illustrates the results of three electrodes that underwent a Type 3 Cyclic Voltammetry Test. A first electrode (Pure Pd) was formed in a roll-to-roll deposition machine with a first zone and a second zone. The first electrode was passed through the first zone to deposit 80% of the electrode's conductive film thickness. Thereafter, the first electrode was passed through the second zone to deposit the remaining 20% of the electrode's conductive film thickness. Each of the first zone and the second zone was filled with an atmosphere comprised essentially of argon (i.e., an inert gas), such that the first electrode was formed by sputtering a palladium target in each of the first and second zones without the introduction of oxygen during the sputtering process. As such, the first electrode was formed essentially of a palladium metal layer on a substrate. Each of the second and third electrodes was formed in a roll-to-roll deposition machine, with a first zone providing a pure argon atmosphere, and a second zone providing a mixed atmosphere of argon/oxygen. As such, each of the second electrode and the third electrode was passed through the first zone to deposit 80% of the electrode's conductive film thickness, and was, thereafter, passed through the second zone to deposit the remaining 20% of the electrode's conductive film thickness. In more detail, the second electrode (PdO 1%) was formed by sputtering a palladium target in the first zone containing the pure argon atmosphere to create the palladium metal layer on a substrate. In addition, the second electrode was formed with a palladium oxide-containing layer on the palladium metal layer by sputtering a palladium target in the second zone containing an argon/oxygen atmosphere mixture containing 1% oxygen. The third electrode was formed by sputtering a palladium target in the first zone containing the pure argon atmosphere to create a palladium metal layer on a substrate. In addition, the third electrode was formed with a palladium oxide-containing layer on the palladium metal layer by sputtering a palladium target in the second zone containing an argon/oxygen atmosphere mixture containing 10% oxygen. None of the electrodes was atmospherically aged before undergoing the Type 3 Cyclic Voltammetry Test.

FIG. 8 shows that the electrodes formed according to embodiments of the present invention, i.e., with a palladium metal layer formed on a substrate and a palladium oxide-containing layer formed on the palladium metal layer, perform electrochemically similar with common redox mediators (e.g., FeIII/II(CN)6 in 0.1 M KCl) as pure palladium electrodes. Because palladium oxide is a semiconductor, and is relatively non-conductive, it is surprising that capping an electrode with a relative semiconductor does not have an effect on the electrochemical performance of the electrode.

Figure 9:
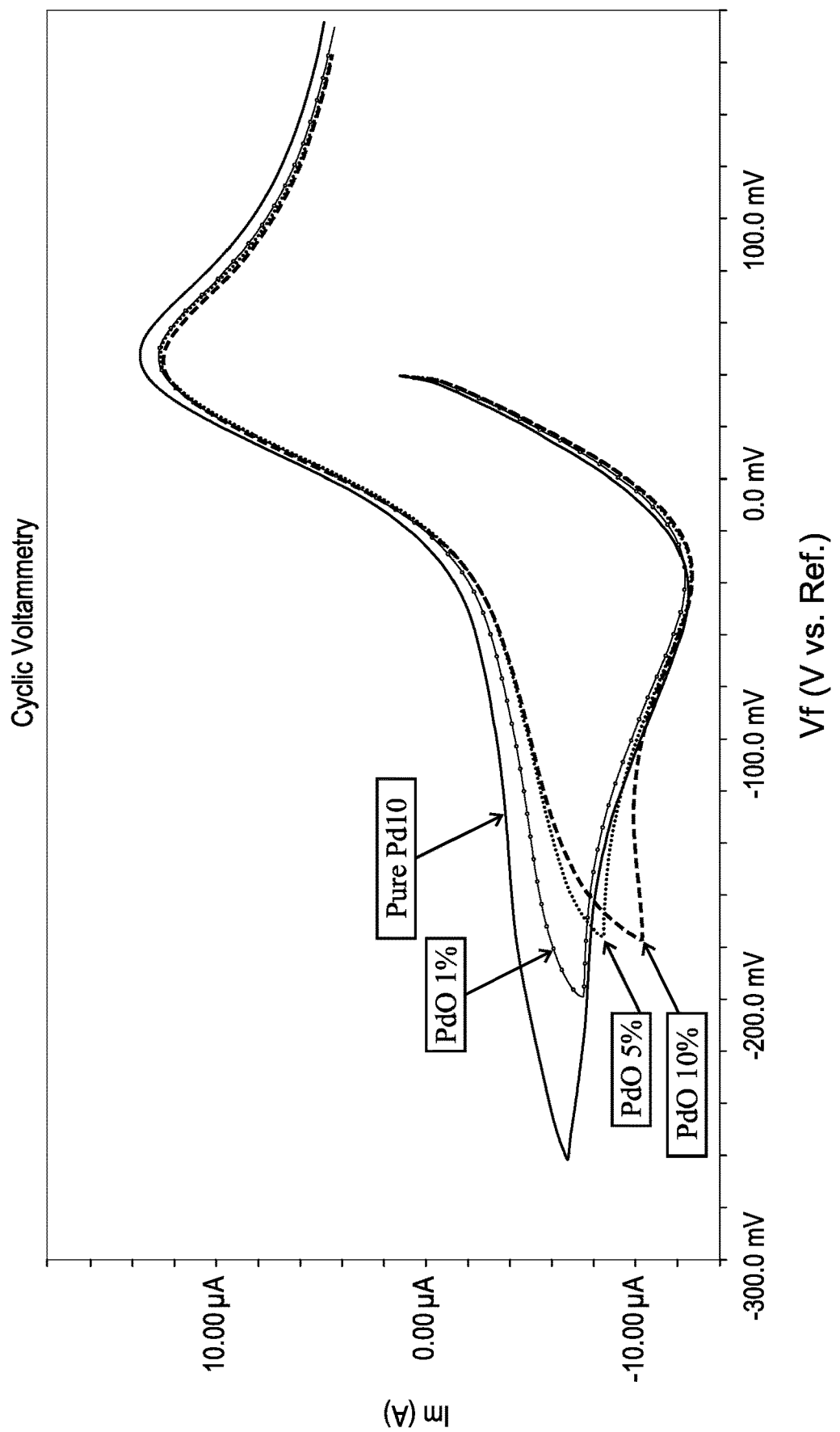
FIG. 9 is a graph depicting a cyclic voltammogram of four electrodes having undergone a Type 4 Cyclic Voltammetry Test.

Experiment of FIG. 9

FIG. 9 illustrates the results of four electrodes that underwent a Type 4 Cyclic Voltammetry Test. A first electrode (Pure Pd10) was formed in a roll-to-roll deposition machine with a first zone and a second zone. The first electrode was passed through the first zone to deposit 80% of the electrode's conductive film thickness. Thereafter, the first electrode was passed through the second zone to deposit the remaining 20% of the electrode's conductive film thickness. Each of the first zone and the second zone was filled with an atmosphere comprised essentially of argon (i.e., an inert gas), such that the first electrode was formed by sputtering a palladium target in each of the first and second zones without the introduction of oxygen during the sputtering process. As such, the first electrode was formed essentially of a palladium metal layer on a substrate. The first electrode was then atmospherically aged for 90 days before undergoing the Type 4 Cyclic Voltammetry Test. Each of the second, third, and fourth electrodes was formed in a roll-to-roll deposition machine, with a first zone providing a pure argon atmosphere, and a second zone providing a mixed atmosphere of argon/oxygen. As such, each of the second electrode, the third electrode, and the fourth electrode was passed through the first zone to deposit 80% of the electrode's conductive film thickness, and was, thereafter, passed through the second zone to deposit the remaining 20% of the electrode's conductive film thickness. In more detail, the second electrode (PdO 1%) was formed by sputtering a palladium target in the first zone comprising the pure argon atmosphere to create a palladium metal layer on a substrate. In addition, the second electrode was formed with a palladium oxide-containing layer on the palladium metal layer by sputtering a palladium target in the second zone comprising an argon/oxygen atmosphere mixture containing 1% oxygen. The third electrode (PdO 5%) was formed by sputtering a palladium target in the first zone containing the pure argon atmosphere to create a palladium metal layer on a substrate. In addition, the third electrode was formed with a palladium oxide-containing layer on the palladium metal layer by sputtering a palladium target in the second zone comprising an argon/oxygen atmosphere mixture containing 5% oxygen. The fourth electrode (PdO 10%) was formed by sputtering a palladium target in the first zone comprising the pure argon atmosphere to create a palladium metal layer on a substrate. In addition, the fourth electrode was formed with a palladium oxide-containing layer on the palladium metal layer by sputtering a palladium target in the second zone comprising an argon/oxygen atmosphere mixture containing 10% oxygen. None of the second, third, or fourth electrodes was atmospherically aged before undergoing the Type 4 Cyclic Voltammetry Test.

FIG. 9 shows that the electrodes formed according to embodiments of the present invention, i.e., with a palladium metal layer formed on a substrate and a palladium oxide-containing layer formed on the palladium metal layer, perform electrochemically similar with common redox mediators (e.g., 3(2',5'-Disulfophenylimino)-3H-phenothiazine in PBS buffer) as pure palladium electrodes that have been atmospherically aged. Because palladium oxide is a semiconductor, and is relatively non-conductive, it is surprising that capping an electrode with a relative semiconductor does not have an effect on the electrochemical performance of the electrode.

Description of MESA Coating Procedure

In addition to beneficial electrochemical properties, the electrodes formed according to embodiments of the present invention are configured to withstand atmospheric aging due to the novel oxide-containing layer formed on the surface of the electrode. As discussed above the extent of oxide surface coverage of an electrode can be quantified by determining the MESA coating properties of the electrode. To measure the MESA coating properties, electrodes can be coated with MESA according to the following MESA Coating Procedure. It should be understood that the following MESA Coating Procedure is similar in certain respects to a procedure described by Macfie et. al. Mechanism of 2-Mercaptoethanesulphonate Adsorption onto Sputtered Palladium Films: Influence of Surface Oxide Species, The Journal of Physical Chemistry C 2012, 116, 9930-9941 (hereinafter Macfie), the entirety of which is incorporated herein by reference.

A first step of the MESA Coating Procedure includes providing a 500 mL beaker containing ~200 mL of a 0.3 mM MESA solution in Milli-Q water. The solution is lightly stirred using a magnetic stirrer, and a 10.16 cm×10.16 cm electrode thin film is placed in the solution for 500 seconds. The electrode thin film is removed, immediately washed with water and ethanol, and air dried. An electrode is cut from the electrode thin film to a size of 5.08 cm×7.62 cm. The electrode is then placed in a 1.0 mM solution of 1-dodecanethiol in ethanol for 16 hrs. Thereafter, the electrode is removed, rinsed with ethanol, dried, and tested for analysis.

Description of Type 1 MESA Coverage Test

The extent of surface MESA coating was calculated using a method similar to that described in Macfie. In more detail, the MESA coated electrodes underwent a Type 3 Voltammetry Test. The voltage difference between the cathodic peak and the anodic peak of the electrode was then determined. In particular, the peak current splitting between the $Fe^{III/II}$ and $Fe^{II/III}$ redox couples ($\Delta E_{peak}$) was determined. As such, $\Delta E_{peak}$ was used in the following equation to determine a fractional surface coverage of MESA (hereinafter defined as "MESA coverage") on the electrode.

$$MESA\ coverage = \left(\frac{\Delta E_{peak}}{0.0198}\right)^{-0.66}$$

Description of Type 1 MESA Kinetics Test

A rate at which MESA was received on the surface of the electrode (hereinafter defined as MESA kinetics) was calculated for each electrode by taking the MESA coverage as calculated from Type 1 MESA Coverage Test and dividing such coverage value by the amount of time the electrode thin film was placed in the MESA solution for coating (i.e., 500 seconds as described in the MESA Coating Procedure).

Applications of MESA Testing

Figure 10:
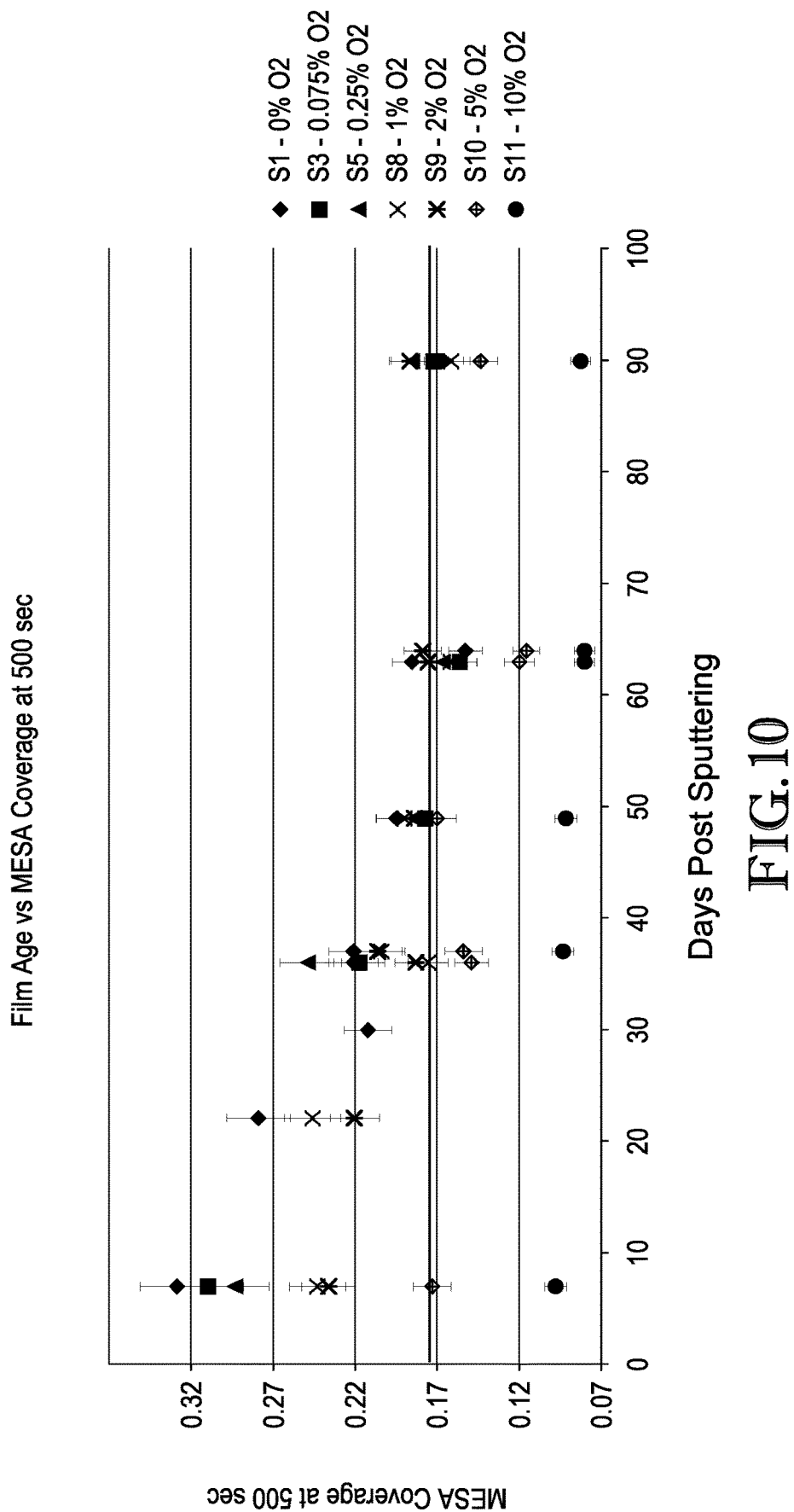
FIG. 10 is a graph depicting MESA coverages of electrodes having undergone a Type 1 MESA Coverage Test.

Experiment of FIG. 10

FIG. 10 illustrates the results of six sets of electrodes that underwent a Type 1 MESA Coating Test. A first set (S1) of electrodes was formed in a roll-to-roll deposition machine with a first zone and a second zone. Each of the electrodes in the first set was passed through the first zone to deposit 80% of the electrode's conductive film thickness. Thereafter, each of the electrodes was passed through the second zone to deposit the remaining 20% of the electrode's conductive film thickness. Each of the first zone and the second zone was filled with an atmosphere comprised essentially of argon (i.e., an inert gas), such that the first set S1 of electrodes were formed by sputtering a palladium target in each of the first and second zones without the introduction of oxygen during the sputtering process. As such, each of the electrodes in the set S1 was formed essentially of a palladium metal layer on a substrate. The remaining electrodes were formed according to embodiments of the present invention in a roll-to-roll deposition machine. In particular, each of the remaining electrodes was formed by sputtering a palladium target in a first zone containing a pure argon atmosphere to create a palladium metal layer on a substrate. Each of such electrodes was sputtered in the first zone such that 80% of the electrode's conductive film thickness was formed in the first zone. In addition, each of the remaining electrodes was formed with a palladium oxide-containing layer on the palladium metal layer by sputtering a palladium target in a second zone comprising an argon/oxygen atmosphere mixture. Specifically, each of such electrodes was sputtered in the second zone such that the remaining 20% of the electrode's conductive film thickness was formed in the second zone. The oxygen percentage (as a partial pressure) in the argon/oxygen atmosphere of the second zone for each remaining electrode sets was as follows:

S3—0.075%;
S5—0.25%;
S8—1.0%;
S9—2.0%;
S10—5.0%; and
S11—10.0%

As shown in FIG. 10, an electrode from each set underwent the MESA Coating Procedure at different times between 7 days post sputtering to 90 days post sputtering. Thereafter, the electrodes underwent the Type 1 MESA Coverage Test to determine the MESA coverage on the electrodes. FIG. 10 illustrates that the MESA coverage of the pure palladium electrodes (i.e., S1), along with the electrodes having their palladium oxide-containing layers formed with low oxygen concentration (e.g., S3, S5, and S8) decrease dramatically over the first 90 days. In contrast, the electrodes having their palladium oxide-containing layer formed with higher oxygen concentrations (e.g., S9, S10, and S11) do not change significantly over the 90 day time period post sputtering. The magenta line in the FIG. 10 represents the MESA coverage of separate, pure palladium electrodes aged for 90 days prior to undergoing the MESA Coating Procedure and the Type 1 MESA Coverage Test. As expected, the MESA coverage of the separate, pure palladium electrodes was consistent over the testing period, as the atmospherically-aged, pure palladium electrode did not experience further oxidation. It was unexpected that the electrodes formed according to embodiments of the present invention, i.e., with a palladium metal layer formed on a substrate and a palladium oxide-containing layer formed on the palladium metal layer, would be more stable to atmospheric aging compared to pure palladium films sputtered in a pure argon atmospheres.

Figure 11:
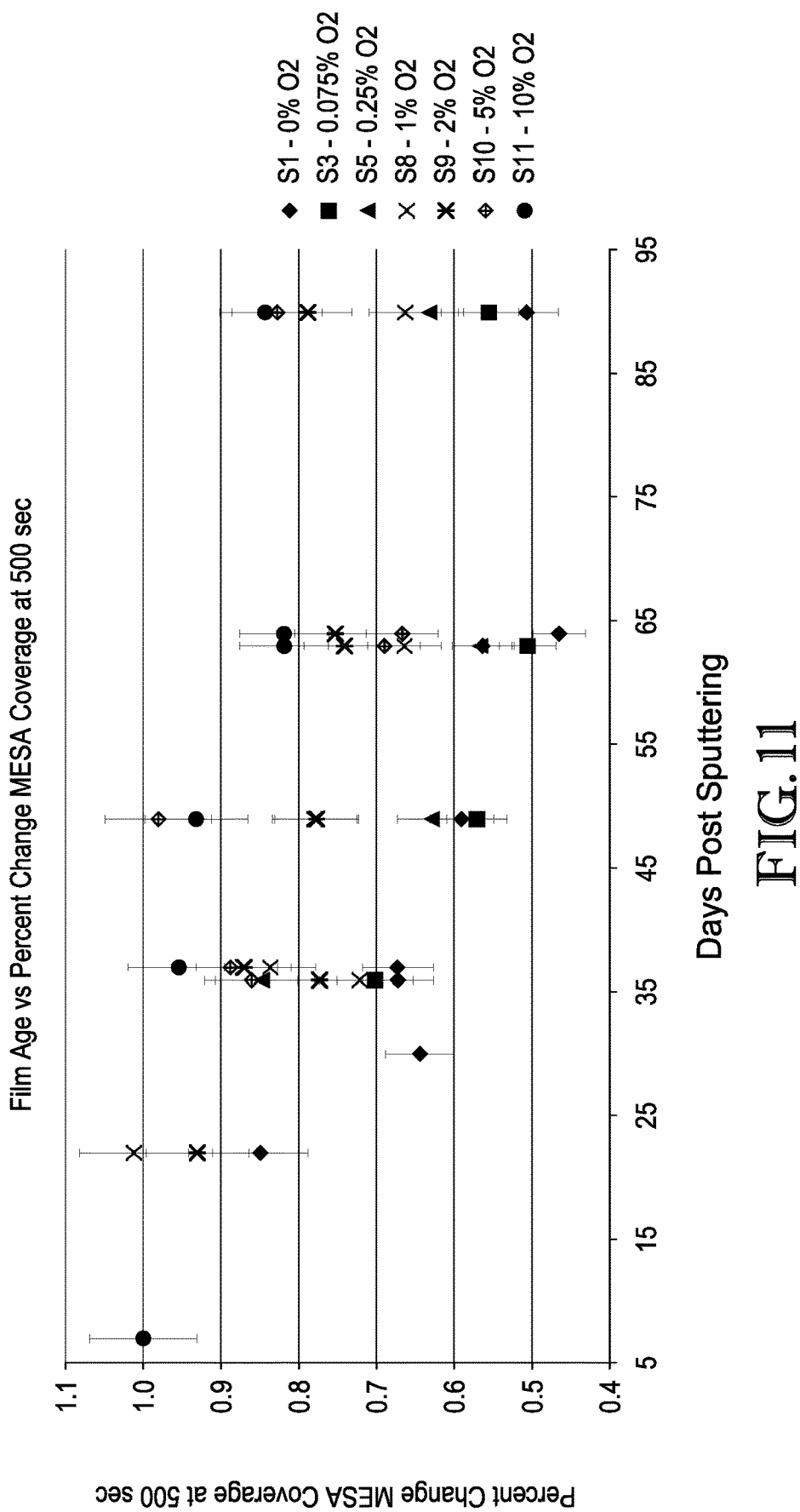
FIG. 11 is a graph depicting MESA coverage percent changes for electrodes having undergone a Type 1 MESA Coverage Test.

Experiment of FIG. 11

FIG. 11 illustrates information from the same electrodes discussed in FIG. 10. However, FIG. 11 illustrates a percent change of MESA coverage from each measurement obtained for a given set of electrodes, with such measurements beginning on day 7 post sputtering and ending on day 90 post sputtering. FIG. 11 shows that the pure palladium electrode sets (i.e., S1) reduce by approximately 50% in MESA coating between day 7 post sputtering and day 90 post sputtering. Such a change is indicative of a significant amount of surface oxidation of the pure palladium electrodes over the time period. In contrast, the electrodes formed according to embodiments of the present invention, i.e., with a palladium metal layer formed on a substrate and a palladium oxide-containing layer formed on the palladium metal layer, had their MESA coatings change by a smaller amount. For example, electrodes from sets S10 and S11 only changed by approximately 15% between day 7 post sputtering and day 90 post sputtering. It was unexpected that electrodes formed according to embodiments of the present invention, i.e., with a palladium metal layer formed on a substrate and a palladium oxide-containing layer formed on the palladium metal layer, would be more stable to atmospheric aging compared to the pure palladium electrodes sputtered in a pure argon atmosphere.

Figure 12:
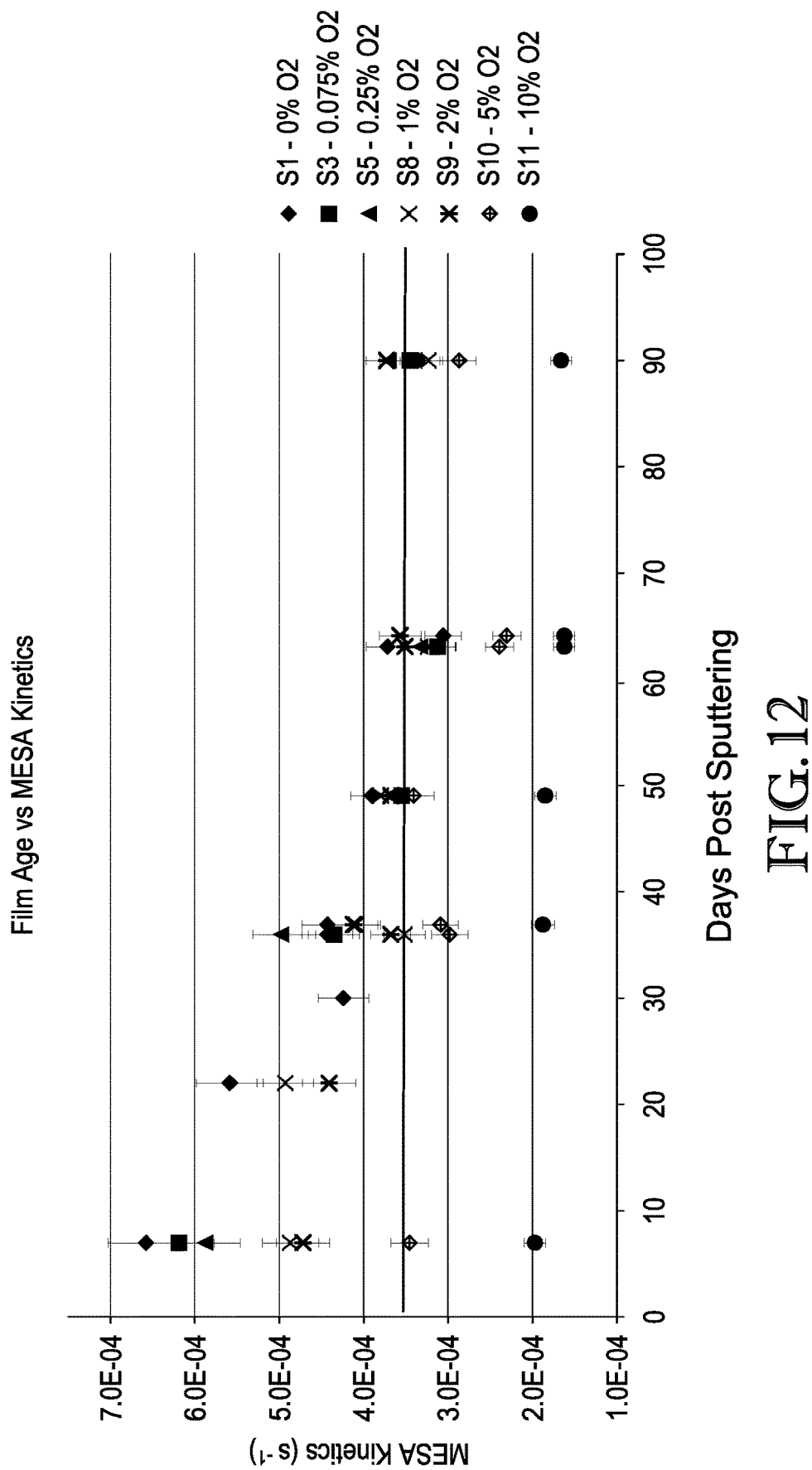
FIG. 12 is a graph depicting MESA kinetics of electrodes having undergone a Type 1 MESA Kinetics Test.

Experiment of FIG. 12

FIG. 12 includes information from the same electrodes discussed in FIGS. 10 and 11. However, in FIG. 12, a Type 1 MESA Kinetics Test was performed on the electrodes to obtain MESA kinetics values for each electrode. FIG. 12 illustrates that the MESA kinetics change with an age of the electrodes. Specifically, FIG. 12 shows that the MESA kinetics of the pure palladium electrode (i.e., S1), along with the electrodes having their palladium oxide-containing layers formed with low oxygen concentration (e.g., S3, S5, and S8) decrease over the first 90 days post sputtering. In contrast, the electrodes having their palladium oxide-containing layer formed with higher oxygen concentrations (e.g., S9, S10, and S11) do not change significantly over the 90 days post sputtering. The magenta line in the plot represents a separate palladium film that was aged for 90 days before its MESA kinetics was measured. FIG. 12 shows that the pure palladium electrodes and the electrodes having their palladium oxide-containing layers formed with low oxygen concentration (e.g., S3, S5, and S8) reach the same MESA kinetics as the separate palladium film that was aged for 90 days. It was unexpected that electrodes formed according to embodiments of the present invention, i.e., with a palladium metal layer formed on a substrate and a palladium oxide-containing layer formed on the palladium metal layer, would be more stable to atmospheric aging compared to the pure palladium electrodes sputtered in a pure argon atmosphere.

Figure 13:
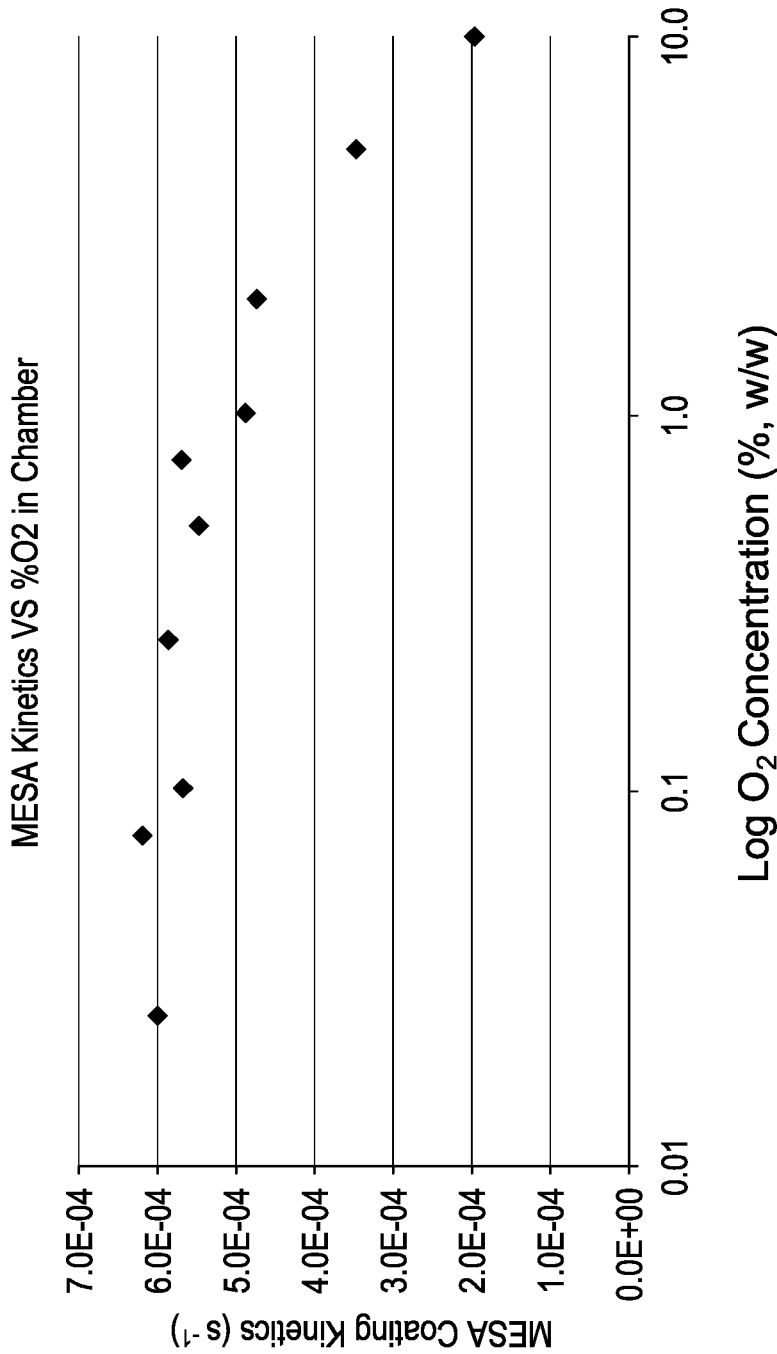
FIG. 13 is another graph depicting MESA kinetics of electrodes having undergone a Type 1 MESA Kinetics Test.

Experiment of FIG. 13

FIG. 13 illustrates how MESA kinetics of electrodes prepared according to embodiments of the present invention, i.e., with a palladium metal layer formed by sputtering in an argon atmosphere and a palladium oxide-containing layer formed on the palladium metal layer by sputtering in an argon/oxygen mixture atmosphere, change based on the concentration of oxygen in the argon/oxygen sputtering atmosphere. In particular, each of the electrodes underwent a type 1 MESA Kinetics Test 6 days post sputtering. FIG. 13 shows that the MESA kinetics, and, thus, the extent of surface oxidation of the electrodes, can be modulated by varying the concentration of oxygen in the argon/oxygen atmosphere. It is unexpected that the extent of oxidation can be modulated to control the kinetics of surface binding of a molecule because the palladium oxide-containing layer structure is different from that of an atmospherically generated palladium oxide.

Figure 14:
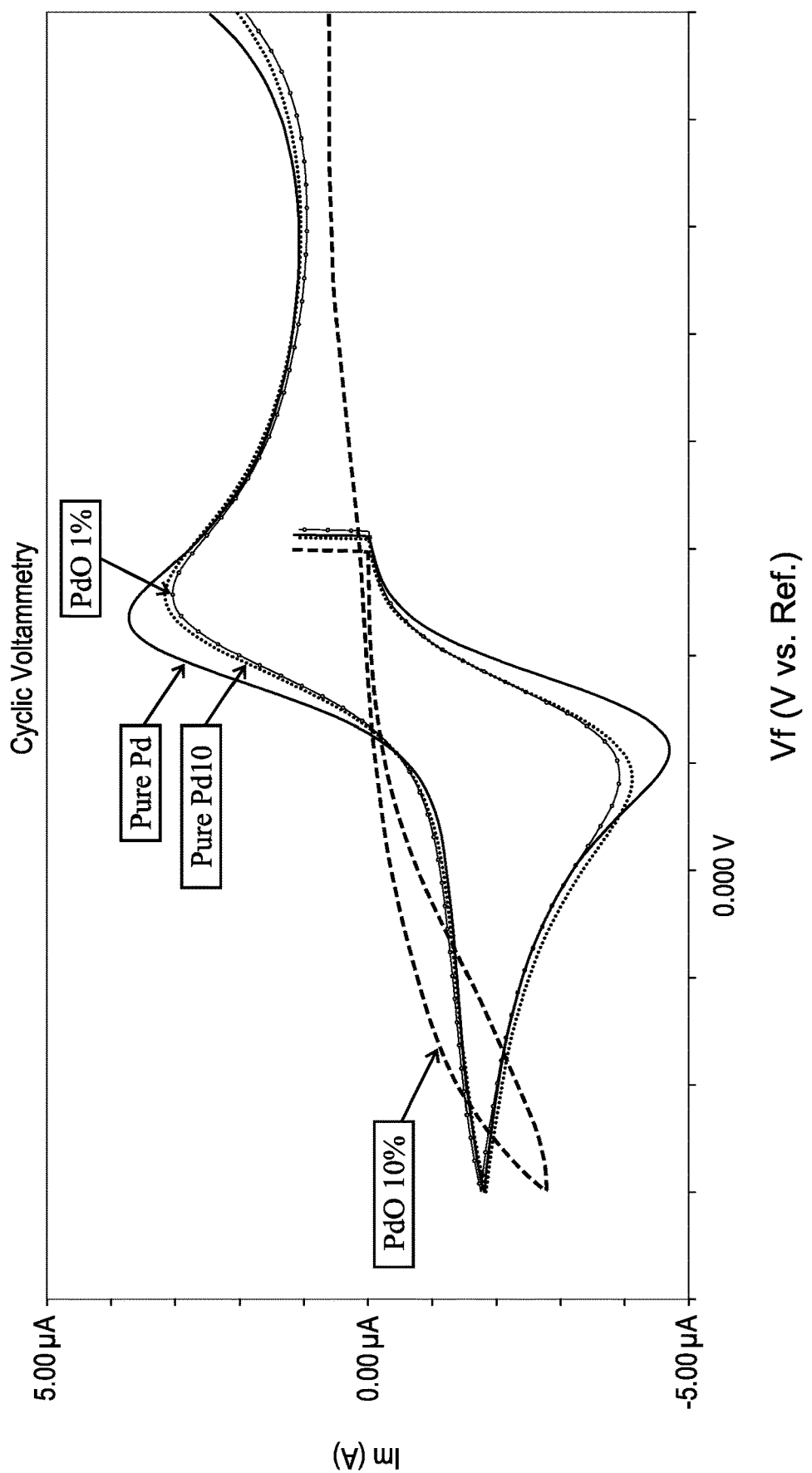
FIG. 14 is a graph depicting a cyclic voltammogram of four electrodes having undergone a Type 3 Cyclic Voltammetry Test.

Experiment of FIG. 14

FIG. 14 illustrates the results of four electrodes that underwent a Type 3 Cyclic Voltammetry Test after being coated by MESA pursuant to the MESA Coating Procedure. A first electrode (Pure Pd) and a second electrode (Pure Pd10) were formed by sputtering a palladium target in a pure argon atmosphere without the introduction of oxygen during the sputtering process. As such, the first electrode and a second electrode were formed essentially of a palladium metal layer on a substrate. The first electrode was atmospherically aged for 1 day and then underwent the MESA Coating Procedure. The second electrode was atmospherically aged for 90 days and then underwent the MESA Coating Procedure. A third electrode (PdO 0.1%) was formed by sputtering a palladium target in a pure argon atmosphere for four minutes to create a palladium metal layer on a substrate. In addition, the third electrode was formed with a palladium oxide-containing layer on the palladium metal layer by sputtering the palladium target in an argon/oxygen atmosphere mixture containing 0.1% oxygen for 1 minute. A fourth electrode (PdO 10%) was formed by sputtering a palladium target in a pure argon atmosphere for four minutes to create the palladium metal layer on the substrate. In addition, the fourth electrode was formed with a palladium oxide-containing layer on the palladium metal layer by sputtering the palladium target in an argon/oxygen atmosphere mixture containing 10% oxygen for 1 minute. The third and fourth electrodes were atmospherically aged for 1 day and underwent the MESA Coating Procedure. Thereafter, each of the electrodes underwent the Type 3 Cyclic Voltammetry Test.

The MESA coating kinetics for the various samples are shown below in Table 1.

TABLE 1

| MESA Coating Kinetics | |
|---|---|
| Sample | Mesa Coating Kinetics ($s^{-1}$) |
| Pd10 (90 days aged) | $5.1 \times 10^{-6}$ |
| No O2 | $6.2 \times 10^{-6}$ |
| 0.1% O2 | $5.2 \times 10^{-6}$ |
| 10% O2 | — |

FIG. 14 shows that the extent of oxidation on the surface of the electrodes can be modulated by changing the oxygen concentration within the argon/oxygen mixture atmosphere during sputtering. In addition, FIG. 14 and Table 1 demonstrate that electrodes formed according to embodiments of the present invention, i.e., with a palladium metal layer formed on a substrate and a palladium oxide-containing layer formed on the palladium metal layer, can match the MESA coating kinetics of 90-day atmospherically aged pure palladium electrodes. It is unexpected that the palladium oxide-containing layers on the electrodes of the present invention dictate the kinetics of surface binding of a small molecule to the surface because the structure of the palladium oxide-containing layers on the electrodes of the present invention are different than that of the atmospherically generated palladium oxide.

The above detailed description of embodiments of the invention is intended to describe aspects of the invention in sufficient detail to enable those skilled in the art to practice the invention. Other embodiments can be utilized and changes can be made without departing from the scope of the invention. The above detailed description is, therefore, not to be taken in a limiting sense. The scope of the present invention is defined only by claims presented in subsequent regular utility applications, along with the full scope of equivalents to which such claims are entitled.

In this description, references to "one embodiment," "an embodiment," or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, step, etc. described in one embodiment may also be included in other embodiments, but is not necessarily included. Thus, the present technology can include a variety of combinations and/or integrations of the embodiments described herein.

The inventors hereby state their intent to rely on the Doctrine of Equivalents to determine and assess the reasonably fair scope of the present invention as it pertains to any apparatus not materially departing from but outside the literal scope of the invention as set forth in the following claims.

Definitions

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "include," and "included" have the same open-ended meaning as "comprising," "comprises," and "comprise" provided above.'

Numerical Ranges

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

What is claimed is:

1. An electrochemical electrode for use in a biosensor, said electrode comprising:
   (a) a substrate;
   (b) a palladium metal layer manufactured on said substrate, wherein said palladium metal layer has a thickness of no more than 90 nm;
   (c) a palladium oxide-containing layer manufactured on said palladium metal layer, wherein said palladium oxide-containing layer has a thickness of at least 0.5 nm and no more than 40 nm;
   a bio-reactant for electrochemically reacting with a biological sample; and
   a mediator.

2. The electrochemical electrode of claim 1, wherein the biosensor is a medical sensor.

3. The electrochemical electrode of claim 2, wherein the medical sensor is a blood glucose sensor.

4. The electrochemical electrode of claim 1, wherein said electrode has a thickness of at least 5 nm and/or not more than 110 nm.

5. The electrochemical electrode of claim 1, wherein said palladium metal layer has a thickness of at least 4 nm and/or not more than 80 nm.

6. The electrochemical electrode of claim 1, wherein said palladium oxide-containing layer has a thickness of at least 0.5 nm not more than 30 nm.

7. The electrochemical electrode of claim 1, wherein said palladium metal layer is sputter coated on said substrate.

8. The electrochemical electrode of claim 1, wherein said palladium oxide-containing layer is sputter coated on said palladium metal layer.

9. The electrochemical electrode of claim 1, wherein said palladium metal layer is sputter coated on said substrate and said palladium oxide-containing layer is sputter coated on said palladium metal layer.

10. The electrochemical electrode of claim 1, wherein said palladium metal layer is sputter coated on the substrate in a first atmosphere consisting essentially of an inert gas;
    wherein the palladium oxide-containing layer is sputtered on the palladium metal layer in a second atmosphere comprising a mixture of the inert gas and an oxidant; and
    wherein the oxidant makes up between 0.5 and 50% of the second atmosphere by partial pressure.

11. The electrochemical electrode of claim 10, wherein the inert gas is argon.

12. The electrochemical electrode of claim 10, wherein the oxidant is selected from one or more of the following: oxygen, ozone, and water.

13. The electrochemical electrode of claim 10, wherein the oxidant is oxygen, and wherein oxygen makes up between 1 and 20% of the second atmosphere by partial pressure.

14. The electrochemical electrode of claim 10, wherein a ratio of the sputtering power used during said sputtering of the palladium metal layer and said sputtering of the palladium oxide-containing layer is about 4:1.

15. The electrochemical electrode of claim 1, wherein said palladium oxide-containing layer has a thickness that is not more than 40% of said palladium metal layer.

16. The electrochemical electrode of claim 1, wherein said substrate comprises a polymeric film.

17. The electrochemical electrode of claim 1, wherein said substrate comprises a polyester or polycarbonate.

18. The electrochemical electrode of claim 1,
    wherein said electrode is configured to receive a particular fractional surface coverage (fractional coverage A) of Mercaptoethanesulphonate (MESA), as determined by the Type 1 MESA Coverage Test, on an outer surface of said electrode upon said electrode being coated in MESA, via a MESA Coating Procedure, within 10 days of said palladium metal layer and said palladium oxide-containing layer being formed,
    wherein said electrode is configured to receive a separate fractional surface coverage (fractional coverage B) of MESA, as determined by the Type 1 MESA Coverage Test, on the outer surface of said electrode upon said electrode being coated in MESA, via the MESA Coating Procedure, after 90 days of said palladium metal layer and said palladium oxide-containing layer being formed,
    wherein the fractional coverage A deviates by no more than 30% from the fractional coverage B.

19. The electrochemical electrode of claim 18, wherein the fractional coverage A deviates by no more than 20% from the fractional coverage B.

* * * * *